(12) United States Patent
Matsubara et al.

(10) Patent No.: US 10,113,147 B2
(45) Date of Patent: Oct. 30, 2018

(54) METHOD FOR PRODUCING MEGAKARYOCYTES, PLATELETS AND/OR THROMBOPOIETIN USING MESENCHYMAL CELLS

(71) Applicant: AdipoSeeds, Inc., Tokyo (JP)

(72) Inventors: Yumiko Matsubara, Tokyo (JP); Takeru Zama, Tokyo (JP); Yasuo Ikeda, Tokyo (JP); Yukako Uruga, Kanagawa (JP); Toshio Suda, Tokyo (JP); Sahoko Matsuoka, Kanagawa (JP)

(73) Assignee: AdipoSeeds, Inc., Tokyo (JP)

( * ) Notice: Subject to any disclaimer, the term of this patent is extended or adjusted under 35 U.S.C. 154(b) by 57 days.

(21) Appl. No.: 14/899,828

(22) PCT Filed: Jun. 27, 2014

(86) PCT No.: PCT/JP2014/003445
§ 371 (c)(1),
(2) Date: Feb. 23, 2016

(87) PCT Pub. No.: WO2014/208100
PCT Pub. Date: Dec. 31, 2014

(65) Prior Publication Data
US 2016/0177265 A1    Jun. 23, 2016

(30) Foreign Application Priority Data

| Jun. 28, 2013 | (JP) | 2013-137004 |
| Jun. 28, 2013 | (JP) | 2013-137033 |
| Mar. 28, 2014 | (JP) | 2014-070058 |

(51) Int. Cl.
*C12N 5/078* (2010.01)
*C07K 14/61* (2006.01)

(52) U.S. Cl.
CPC ............ *C12N 5/0644* (2013.01); *C07K 14/61* (2013.01); *C12N 2500/24* (2013.01); *C12N 2501/145* (2013.01); *C12N 2506/13* (2013.01); *C12N 2506/1384* (2013.01); *C12N 2511/00* (2013.01)

(58) Field of Classification Search
None
See application file for complete search history.

(56) References Cited

U.S. PATENT DOCUMENTS

| 6,225,119 B1 * | 5/2001 | Qasba ............... | C12N 5/0644 424/93.2 |
| 2010/0112697 A1 * | 5/2010 | Kim ................... | C12N 5/0605 435/381 |

FOREIGN PATENT DOCUMENTS

JP    2000-083656    3/2000

OTHER PUBLICATIONS

Al-Nbaheen et al. "Human stromal (mesenchymal) stem cells from bone marrow, adipose tissue and skin exhibit difference in molecular phenotype and differentiation potential", Stem Cell Reviews and Reports 9: 32-43, published online Apr. 14, 2012 (Year: 2012).*
Ono et al. "Pre-Adipocytes Differentiate Into Megakaryocytes (MK) by a Paracrine Thrombopoietin (TPO) Loop." Blood 120: 4742, 2012 (Year: 2012).*
International Preliminary Report on Patentability for PCT/JP2014/003445, dated Jan. 7, 2016.
Burstein et al., "Leukemia inhibitory factor and interleukin-11 promote maturation of murine and human megakaryocytes in vitro," *Journal of Cellular Physiology*, 153(2):305-312, 1992.
De Sauvage et al., "Stimulation of megakaryocytopoiesis and thrombopoiesis by the c-Mpl ligand," *Nature*, 369:533-538, 1994.
Freireich et al., "Origins of platelet transfusion therapy," *Transfusion Medicine Reviews*, 25(3):252-256, 2011.
Gaur et al., "Megakaryocytes derived from human embryonic stem cells: a genetically tractable system to study megakaryocytopoiesis and integrin function," *Journal of Thrombosis Haemostasis*, 4(2):436-442, 2006.
Kappers et al., "Serum thrombopoietin levels in relation to disease status in patients with immune thrombocytopenic purpura," *British Journal of Haematology*, 115:1004-1006, 2001.
Kaushansky, "Thrombopoietin," *The New England Journal of Medicine*, 339:746-754, 1998.
Kuter, "Future directions with platelet growth factors," *Semin Hematol.*, 37(2 Suppl. 4):41-49, 2000.
Kuter et al., Recombinant human thrombopoetin: basic biology and evaluation of clinical studies. *Blood*, 100: 3457-3469, 2002.
Matsubara et al., "Generation of megakaryocytes and platelets from human subcutaneous adipose tissues," *Biochemical and Biophysical Research Communications*, 378:716-720, 2009.
Matsubara et al., "Generation of megakaryocytes and platelets from preadipocyte cell line 3T3-L1, but not the parent cell line 3T3, in vitro" *Biochemical and Biophysical Research Communications*, 402:796-800, 2010.

(Continued)

*Primary Examiner* — Emily A Cordas
(74) *Attorney, Agent, or Firm* — Occhiuti & Rohlicek LLP

(57) ABSTRACT

Provided is a megakaryocyte and/or platelet production method, enabling to produce a megakaryocyte and/or platelet from mesenchymal cells such as preadipocytes in a relatively short period of time, simply, in a large amount and at lower cost or more efficiently in vitro and a method for producing TPO simply and in a larger amount. A first invention is a method for producing a megakaryocyte and/or platelet, comprising culturing a mesenchymal cell in a mesenchymal cell culturing basic medium containing an iron ion and an iron transporter and collecting megakaryocytes and/or platelets from a culture. A second invention is a method for producing thrombopoietin, comprising culturing a mesenchymal cell or mesenchymal cell-derived megakaryocyte in a mesenchymal cell culturing basic medium containing an iron ion and an iron transporter and collecting thrombopoietin from a culture. A third invention is a method for producing thrombopoietin, comprising culturing a preadipocyte in a preadipocyte culturing basic medium containing dexamethasone, 3-isobutyl-1-methylxanthine and insulin and collecting thrombopoietin from a culture.

13 Claims, 7 Drawing Sheets

Specification includes a Sequence Listing.

(56) References Cited

OTHER PUBLICATIONS

Matsubara et al., "Culture of megakaryocytes and platelets from subcutaneous adipose tissue and a preadipocyte cell line," *Methods in Molecular Biology*, 788:249-258, 2012.

Nakamura et al., "Expandable megakaryocyte cell lines enable clinically applicable generation of platelets from human induced pluripotent stem cells," *Stem Cells* 14:535-548, 2014.

Ono et al., "Induction of functional platelets from mouse and human fibroblasts by p45NF-E2/Maf," *Blood*, 120(18):3812-3821, 2012.

Reems et al., "In vitro megakaryocyte production and platelet biogenesis: state of the art," *Transfusion Med. Rev.*, 24(1):33-43, 2010.

Shandadfar et al., "In vitro expansion of human mesenchymal stem cells: choice of serum is a determinant of cell proliferation, differentiation, gene expression, and transcriptome stability," *Stem Cells*, 23:1357-1366, 2005.

Stroncek et al., "Platelet transfusions," *The Lancet*, 370:427-438, 2007.

Takayama et al., "Generation of functional platelets from human embryonic stem cells in vitro via ES-sacs, VEGF-promoted structures that concentrate hematopoietic progenitors," *Blood*, 111:(11):5298-5306, 2008.

Takayama et al., "Transient activation of c-MYC expression is critical for efficient platelet generation from human induced pluripotent stem cells," *Journal of Experimental Medicine*, 207(13):2817-2830, 2010.

Teramura et al., "Clonal growth of human megakaryocyte progenitors in serum-free cultures: effect of recombinant human interleukin 3," *Exp Hematol.* 16:843-848, 1988.

Teramura et al., "Effect of recombinant hemopoietic growth factors on human megakaryocyte colony formation in serum-free cultures," *Exp Hematol.*, 17:1011-1016, 1989.

Teramura et al., "The effect of cytokines on the ploidy of megakaryocytes," *International Journal of Cell Cloning*, 8:245-252, 1990.

Teramura et al., "Interleukin-11 enhances human megakaryocytopoiesis in vitro," *Blood*, 79:327-331, 1992.

The Mainichi, "iPS cell: preparation of platelet in large amount," Dec. 11, 2011, p. 30, Retrieved fromG-Search. (English Abstract included.).

Vadhan et al., "Recombinant human thrombopoietin attenuates carboplatin-induced severe thrombocytopenia and the need for platelet transfusions in patients with gynecologic cancer," *Ann. Intern. Med.* 132:364-368, 2000.

Vadhan et al., "Importance of predosing of recombinant human thrombopoietin to reduce chemotherapy-induced early thrombocytopenia," *Journal of Clinical Oncology*, 21:3158-3167, 2003.

Williams et al., "Two-factor requirement for murine megakaryocyte colony formation," *Journal of Cellular Physiology*, 110:101-104, 1982.

Ondo et al., "Pre-Adipocytes Differentiate Into Megakaryocytes (MK) by a Paracrine Thrombopoietin (TPO) Loop," Blood (ASH Annual Meeting Abstracts) 120: Abstract 4742, 2012.

Kaszubska, Wiweka, Haiying Zhang, Robert L. Patterson, Thomas S. Suhar, Marie E. Uchic, Robert W. Dickinson, Verlyn G. Schaefer et al. "Expression, purification, and characterization of human recombinant thrombopoietin in Chinese hamster ovary cells." Protein expression and purification 18, No. 2 (2000): 213-220.

\* cited by examiner

[Figure 1]
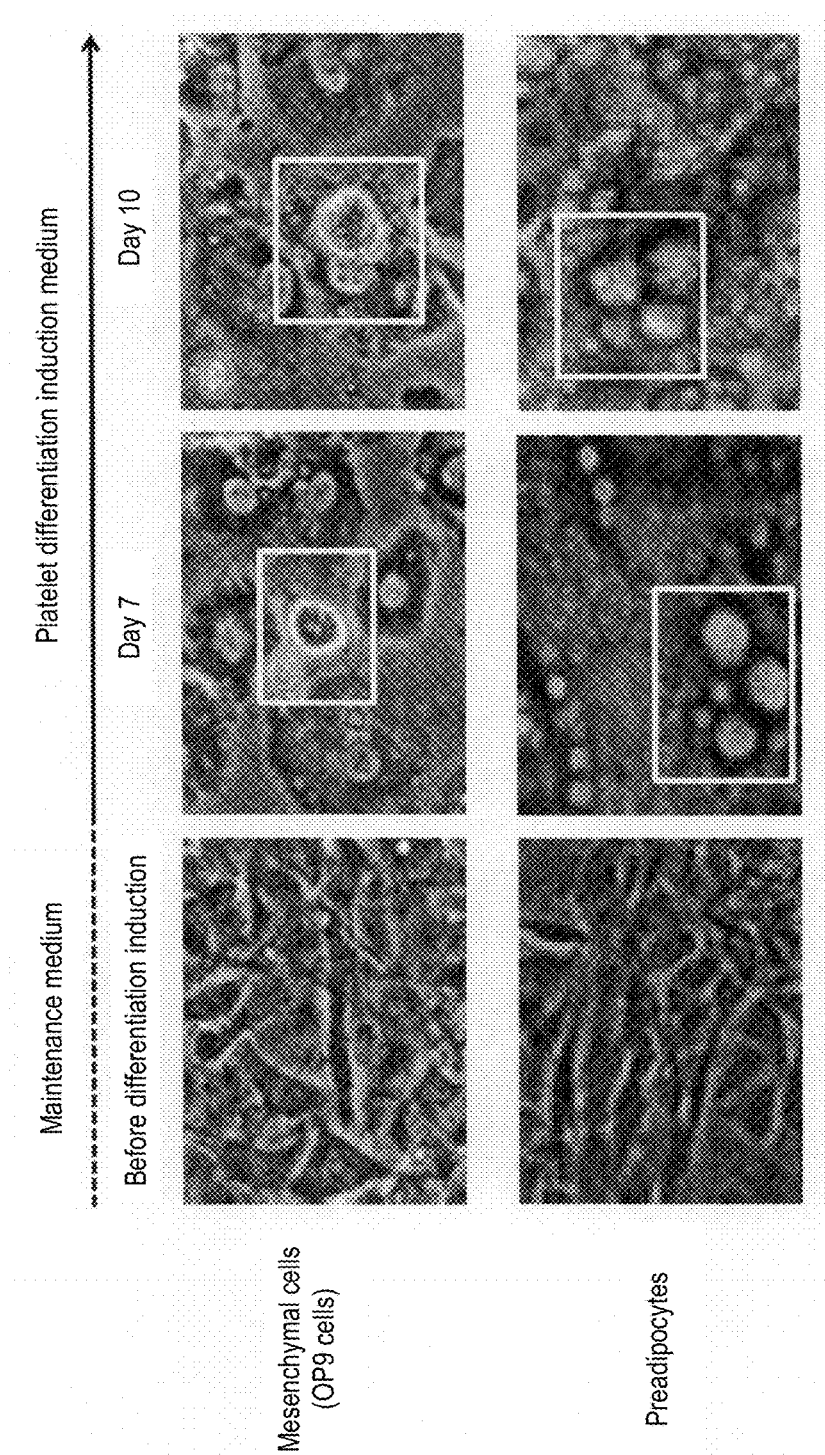

[Figure 2]
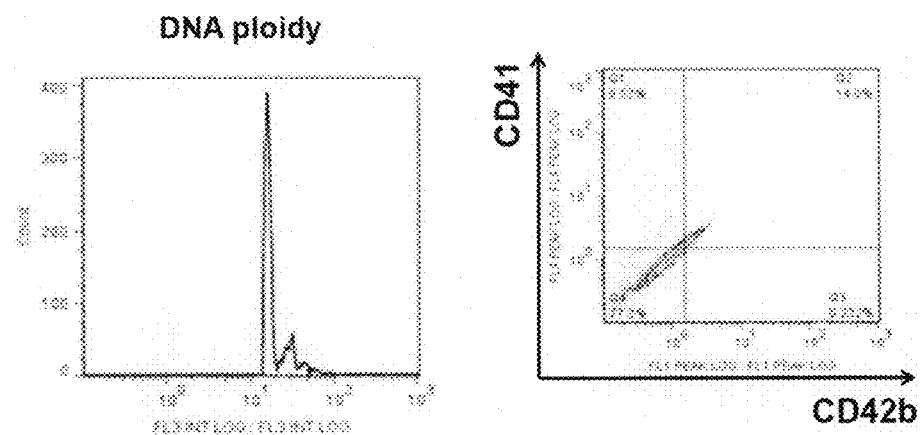
[Figure 3]
Total Thrombus-formation Analysis System (Thrombus formation analysis in blood flow)
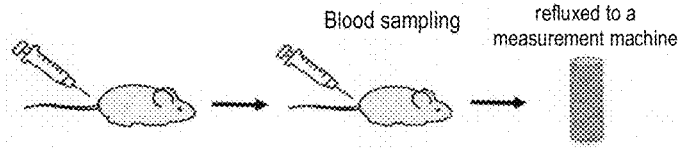

[Figure 4]
After reflux of blood sample taken from a thrombocytopenia mouse
transfused with megakaryocytes produced from preadipocytes
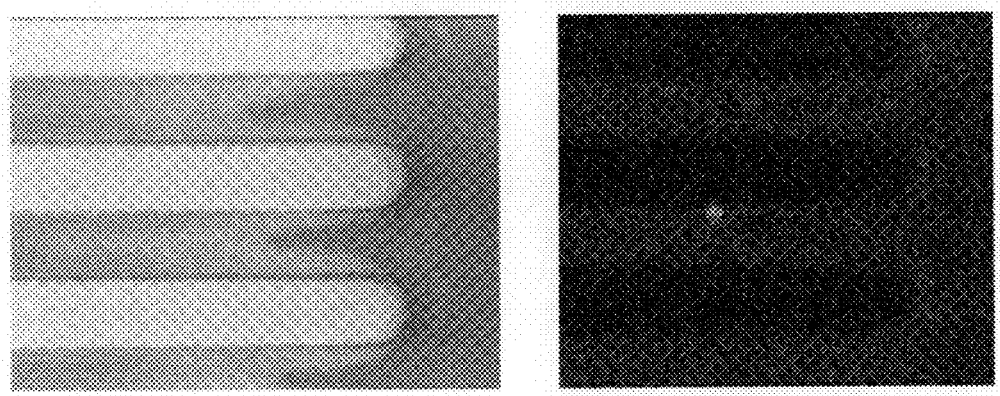
Thrombus measurement          After refluxing blood taken from
chips before sample reflux        thrombocytopenia mouse
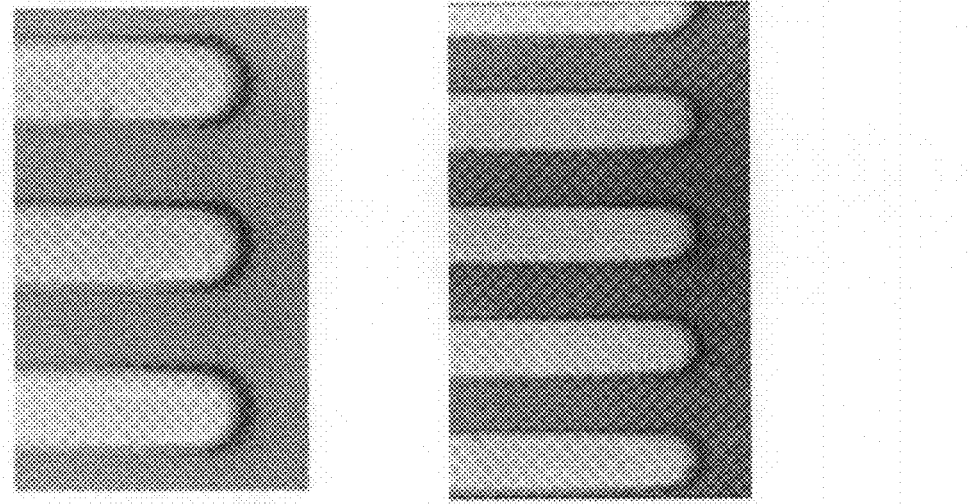

[Figure 5]
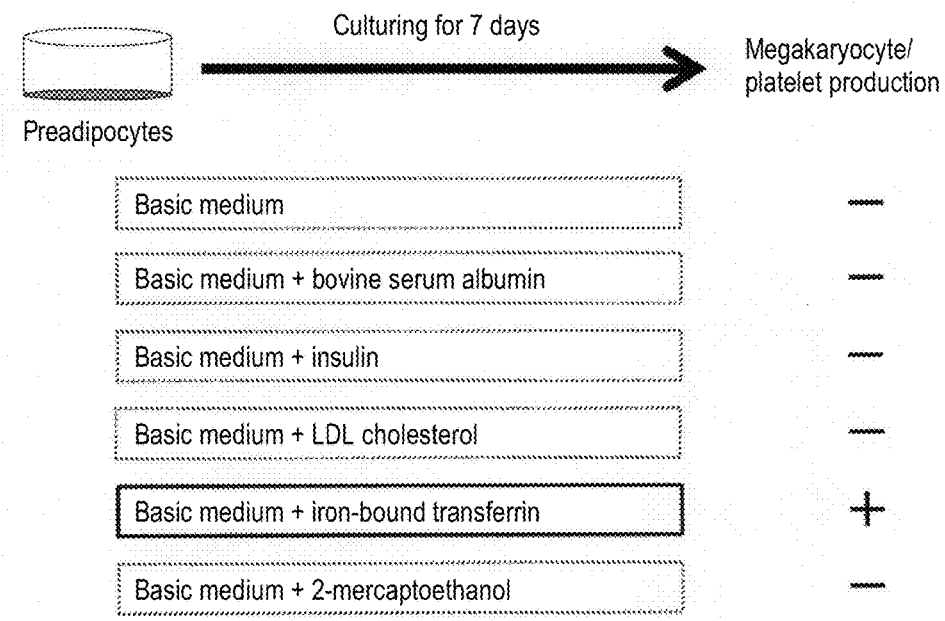
[Figure 6]
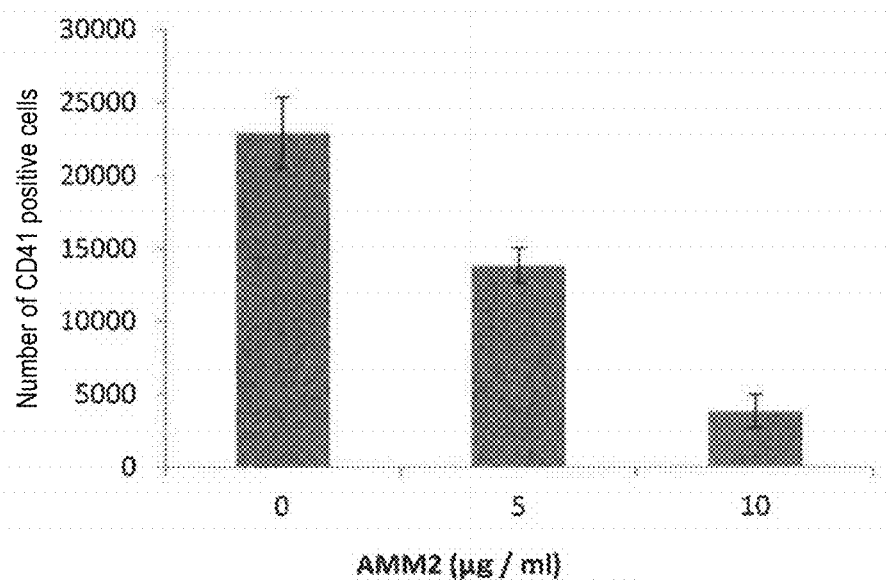
Investigation of effect of AMM2 on differentiation induction of preadipocytes

[Figure 7]
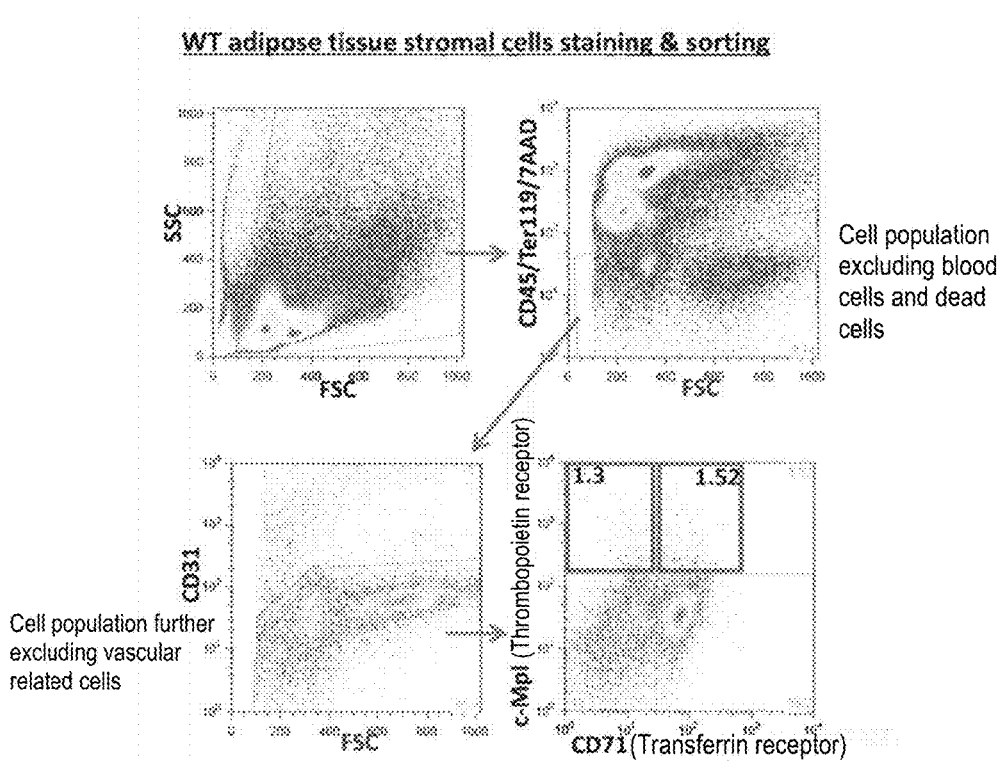

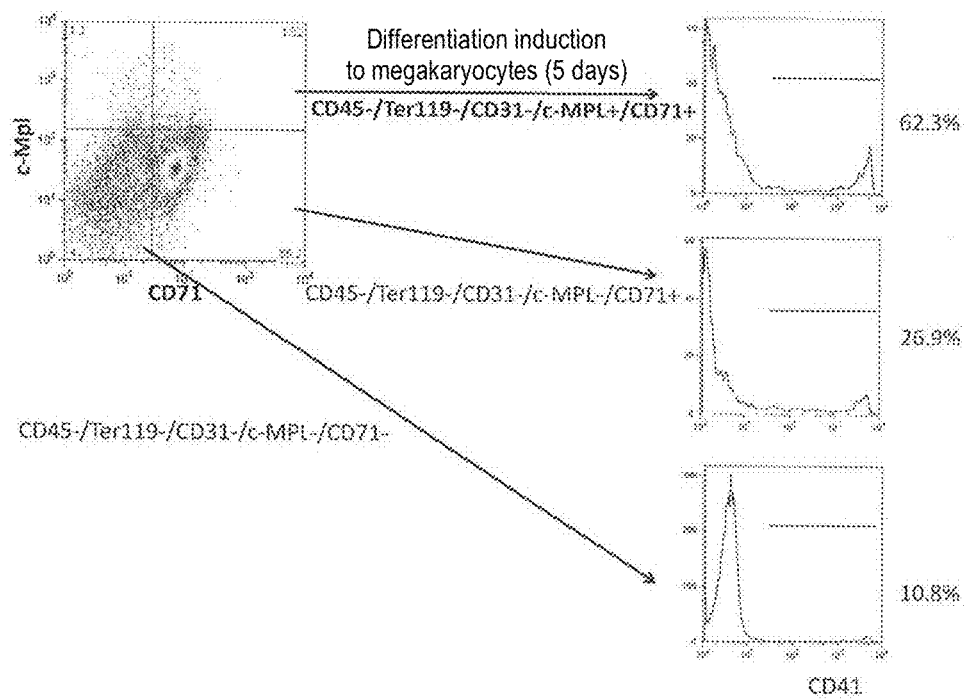
[Figure 8]

[Figure 9]
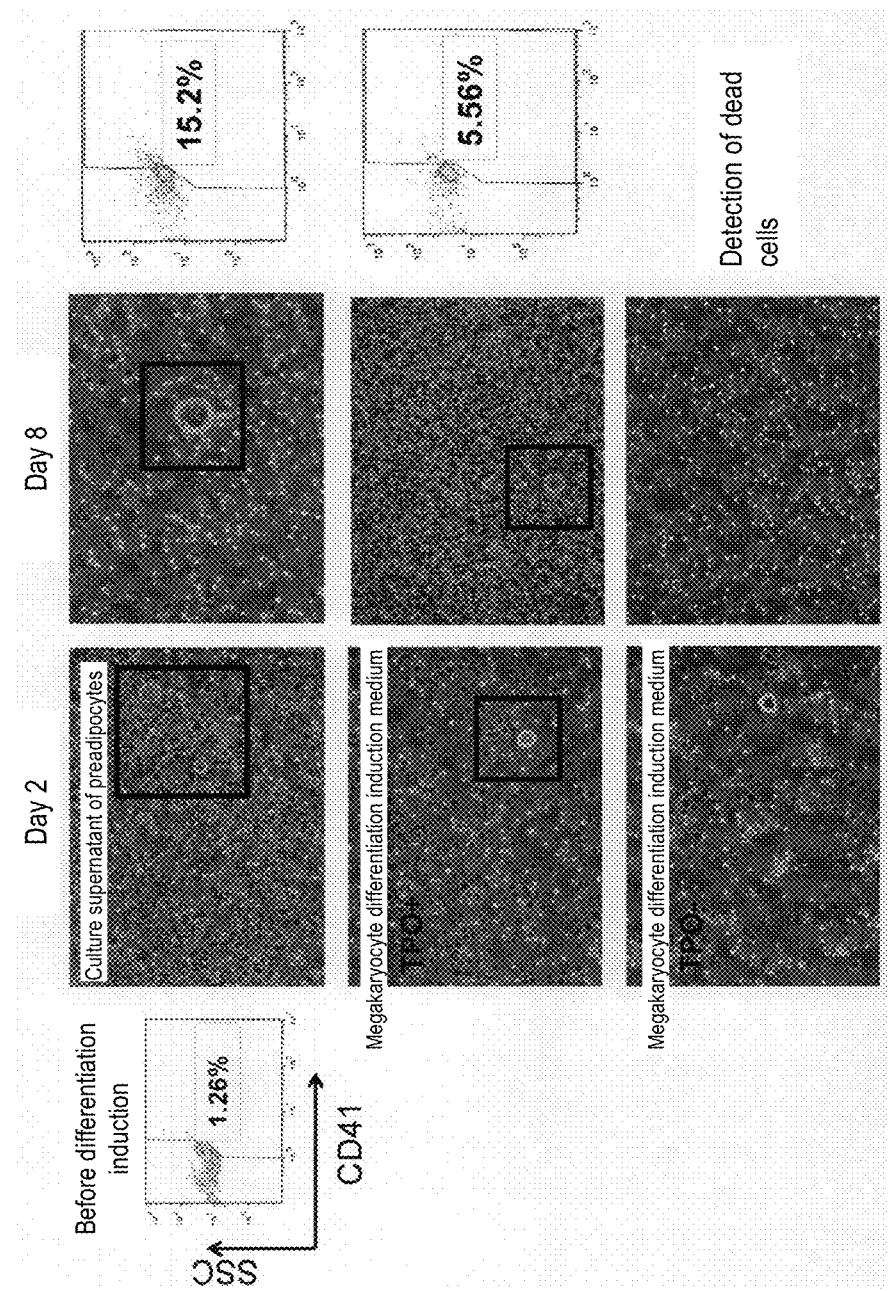

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: siRNA-CD71 sense
<220> FEATURE:
<221> NAME/KEY: misc_feature
<223> OTHER INFORMATION: Inventor: MATSUBARA, Yumiko; ZAMA, Takeru;
      IKEDA, Yasuo; URUGA, Y ukako; SUDA, Toshio; MATSUOKA, Sahoko

<400> SEQUENCE: 1
gaacuugaaa cugcguaaat t                                             21

<210> SEQ ID NO 2
<211> LENGTH: 21
<212> TYPE: DNA
<213> ORGANISM: Artificial
```

```
<220> FEATURE:
<223> OTHER INFORMATION: siRNA-CD71 antisense

<400> SEQUENCE: 2
uuuacgcagu uucaaguuct t                                              21

<210> SEQ ID NO 3
<211> LENGTH: 21
<212> TYPE: DNA
<213> ORGANISM: Artificial
<220> FEATURE:
<223> OTHER INFORMATION: negative control sense

<400> SEQUENCE: 3
ucuuaaucgc guauaaggct t                                              21

<210> SEQ ID NO 4
<211> LENGTH: 21
<212> TYPE: DNA
<213> ORGANISM: Artificial
<220> FEATURE:
<223> OTHER INFORMATION: negative control antisense

<400> SEQUENCE: 4
gccuuauacg cgauuaagat t                                              21
```

METHOD FOR PRODUCING MEGAKARYOCYTES, PLATELETS AND/OR THROMBOPOIETIN USING MESENCHYMAL CELLS

CROSS REFERENCE TO RELATED APPLICATIONS

This application is a U.S. national phase application filed under 35 USC § 371 of International Application No. PCT/JP2014/003445, filed Jun. 27, 2014, which claims the benefit of the priority date of Japanese Application No. 2013-137004, filed Jun. 28, 2013, Japanese Application No. 2013-137033, filed Jun. 28, 2013, and Japanese Application No. 2014-070058, filed Mar. 28, 2014. The contents of the aforementioned applications are incorporated by reference herein in their entirety.

TECHNICAL FIELD

The present invention relates to a method for producing megakaryocytes/platelets and/or thrombopoietin (TPO), and more specifically, to a method for producing megakaryocytes, platelets and/or TPO by culturing mesenchymal cells having a predetermined cell-surface marker profile in a medium containing an iron ion and an iron transporter and collecting megakaryocytes, platelets and/or TPO from a culture.

BACKGROUND ART

Platelet transfusion is only one therapy against platelet depletion caused by e.g., bleeding associated with accidents and during use of anti-cancer agents. Platelet preparations to be used for the time are produced completely (100%) depending upon blood donation with good intentions, at present. Platelets are very fragile and a method enabling platelets for use in therapy to store for a long time has not yet been developed. Actually, it is reported that the storage life of platelets in the latest medical institutions is four days; however, in consideration of time required for inspection and shipment, substantial storage life thereof in clinical sites including clinics is conceivably about three days. Likewise, many blood banks have a difficulty in storing platelets while keeping freshness at all times. In addition, the supply amount of platelet preparations is likely to vary dependent upon a decrease of blood donors and an increase of blood donors affected with viral infectious diseases (non-patent documents 1, 2).

In the circumstances, recently, a novel platelet supply source has attracted attention, which has been developed in place of blood donation having such problems (non-patent document 3). As an example, development of a technique of producing a large amount of platelets in vitro using somatic stem cells, i.e., hematopoietic stem cells (umbilical cord blood stem cells) is known. However, this technique has not yet been put into practical use, because an in vitro method for proliferating hematopoietic stem cells per se has not yet been established. In contrast, pluripotent stem cells, i.e., embryonic stem (ES) cells have an advantage in that they can be unlimitedly proliferated in vitro and have attracted attention as a supply source for producing blood cells including platelets. In this respect, techniques for producing mature megakaryocytes and platelets from human ES cells have been already reported (non-patent documents 4, 5). However, in the techniques (methods), the production efficiency of platelets is low and tens of thousands of petri dishes are required for producing a single blood transfusion preparation. These methods were insufficient from a practical point of view.

In transfusion of platelets, refractory to platelet transfusion is raised as a problem. At the first-time transfusion, platelets having a different human leukocyte antigen (HLA) from a patient can be used; however, a specific antibody against the HLA is produced in the patient's body when transfusion is repeated, with the result that the platelets are rejected immediately upon transfusion. In addition, since platelets have own blood type, i.e., an allogeneic human platelet antigen (HPA), refractory to transfusion caused by incompatibility of HPA types is also known. As a technique which can overcome this problem, techniques for producing megakaryocytes and platelets from human induced pluripotent stem (iPS) cells have been reported (non-patent documents 6, 7). For example, if platelets are induced from a patient-derived iPS cells, it is theoretically possible to produce a rejection-free custom-made platelet preparation. However, in producing platelets from iPS cells, at least about 50 days are required for producing platelets from fibroblasts (non-patent documents 6, 7). For the reason, this production method was insufficient from a practical point of view. In the meantime, as a method for producing platelets from fibroblasts, a technique called direct reprogramming is known (non-patent document 8). According to this technique, the period required for producing platelets will be greatly shorter than the method for producing platelets via iPS cells. Advantageously, platelets are produced in about 14 days. However, the direct reprogramming using fibroblasts requires gene introduction. The effect of the presence of a gene transfer vector on safety is concerned.

As a culture medium for inducing differentiation of hematopoietic stem cells into megakaryocytes/platelets, MKLI medium (megakaryocyte lineage induction medium) is known. The MKLI medium is a medium prepared by adding, 2 mM L-glutamine, a 100 U/mL penicillin-streptomycin solution, 0.5% bovine serum albumin, 4 μg/mL LDL cholesterol, 200 μg/mL iron-saturated transferrin (iron-bound transferrin), 10 μg/mL insulin, 50 μM 2-β-mercaptoethanol, nucleotides (20 μM for each of ATP, UTP, GTP and CTP) and 50 ng/mL thrombopoietin (thrombopoietin: TPO) to Iscove's Modified Dulbecco's Medium (IMDM) (non-patent document 9). The present inventors have so far conducted studies on a technique for inducing differentiation of cells excluding hematopoietic stem cells into megakaryocytes/platelets. As a result, they have found that if preadipocytes derived from a human subcutaneous adipose tissue (non-patent documents 9, 10) and mouse-derived preadipocytes (non-patent documents 9, 11) are cultured in the MKLI medium, they can be differentiated into megakaryocytes/platelets. In these methods using preadipocytes, platelets can be efficiently produced in vitro in a relatively short period of time. In addition, these methods do not require gene introduction and they are excellent in safety when the platelets are administered to patients. In the context, a method for preparing megakaryocytes and platelets at lower cost or more efficiently has been desired.

"Platelets" is one of material components in blood and plays a major role in arresting bleeding in living bodies. If abnormal clump of platelets is formed, thrombotic diseases are caused. Platelets are also involved in metastasis and growth of cancer. The role of platelets has recently attracted attention in a wide variety of fields. Platelets are developed from hematopoietic stem cells in the bone marrow through the following step. The hematopoietic stem cells are developed into megakaryocyte lineage progenitor cells and then into megakaryoblasts, which are further matured into megakaryocytes. Thereafter, the cytoplasm of megakaryocytes is torn apart into several thousands of pieces and released into blood. It has been considered that, in order to form megakaryocyte colonies from hematopoietic stem cells in the bone marrow, two types of factors having different actions are required (non-patent document 12), more specifically, Meg-CSF, which supports colony formation by itself, and Meg-POT, which does not functionally support formation of colonies but promotes maturation of megakaryocytes in the presence of Meg-CSF. As the factor having Meg-CSF activity in human, e.g., IL-3 (non-patent document 13) and GM-CSF (non-patent document 14), are known. As the factor having Meg-POT activity in human, e.g., IL-6 (non-patent document 15), IL-11 (non-patent document 16) and LIF (non-patent document 17) are known.

However, these are all not specific factors to the megakaryocyte/platelet lineage but factors known to act on other hematocyte system and cells other than hematocytes. Thus, if these are administered as pharmaceutical products in expectation of action on the megakaryocyte/platelet lineage, it is concerned that another action is expressed against expectation. In the context, a physiologically active substance specifically acting on megakaryocyte/platelet lineage and extremely useful as a pharmaceutical product has been strongly desired. As a factor specifically acting on the megakaryocyte/platelet lineage, a human c-MPL receptor ligand, TPO, is known and a gene of TPO has been cloned (non-patent document 18). The c-MPL protein is a glycoprotein, which expresses on hematopoietic stem cells and megakaryocyte lineage cells and belongs to a cytokine receptor gene family. It has been suggested that the c-MPL protein is deeply involved in platelet production as a receptor for a novel factor involved in platelet production. TPO cloned has both Meg-CSF activity and Meg-POT activity and serves as a specific factor to the megakaryocyte/platelet lineage.

TPO is an important regulatory factor of platelet production and stimulates growth of megakaryocytes producing platelets and production of platelets from megakaryocytes (non-patent document 19). TPO is synthesized in the liver as a proprotein consisting of 353 amino acids and becomes a mature protein molecule by cleaving a signal peptide of 21 amino acids. The mature protein molecule consists of two domains having a high homology with erythropoietin and a highly glycosylated carboxy terminal important for protein stability (non-patent document 20). An increase of TPO level is not observed in patients with immune thrombocytopenic purpura (ITP) (non-patent document 21). The need for mass production and purification of TPO has been insisted for developing a drug for increasing platelets; however, since TPO is consistently produced from major TPO-producing cells, i.e., hepatocytes, in an extremely low amount, supplying purified TPO endogenously produced in a large amount has not been achieved.

In the context, studies on recombinant TPO have been conducted and two types of recombinant TPO molecules have been subjected in a large-scale clinical trial. One is recombinant human TPO (referred to also as either rHuTPO or rHTPO), which is a glycosylated molecule having the same full-length amino acid sequence as in natural TPO. The other one is a non-glycosylated molecule containing 1-163 amino acids corresponding to a biologically active domain of natural TPO, namely a polyethylene glycol (PEG)-bound recombinant human megakaryocyte growth and development factor (PEG-rHuMGDF) (non-patent documents 19, 20, 22). Both recombinant TPO molecules are potent stimulatory substances for platelet production in human and have an ability to mitigate thrombocytopenia caused by chemical therapy and are useful for reducing necessity of platelet transfusion (non-patent documents 23, 24). In the context, an attempt to express a full length recombinant human TPO (rHuTPO) has been made using cultured cells; however, glycosylation of the resultant TPO was different from endogenous TPO. Thus, a technology for producing TPO having an ability to induce/promote platelet production by such a method has not yet been established. It was also found in clinical researches conducted over the past decade that PEG-rHuMDGF induces an antibody that cross-reacts with endogenous TPO, and induces thrombocytopenia in 4% of healthy individuals and 0.6% of cancer patients who received intensive chemotherapy (non-patent document 22).

In such technological circumstances, practical technologies for TPO production, such as TPO production using hepatocytes and recombinant TPO production without the aforementioned problems, have been desired.

As a medium capable of inducing differentiation of hematopoietic stem cells into megakaryocytes/platelets, MKLI medium (megakaryocyte lineage induction medium) is known. The MKLI medium is a medium prepared by adding 2 mM L-glutamine, a 100 U/mL penicillin-streptomycin solution, 0.5% bovine serum albumin, 4 µg/mL LDL cholesterol, 200 µg/mL iron-saturated transferrin (iron-bound transferrin), 10 µg/mL insulin, 50 µM 2-β-mercaptoethanol, nucleotides (20 µM each for ATP, UTP, each GTP and CTP) and 50 ng/mL TPO to Iscove's Modified Dulbecco's Medium (IMDM) (non-patent document 9). The present inventors have so far conducted studies on a technology for inducing differentiation of cells excluding hematopoietic stem cells into megakaryocytes/platelets, and have found that if human preadipocytes derived from a subcutaneous adipose tissue (non-patent documents 9, 10) and mouse-derived preadipocytes (non-patent documents 9, 11) are cultured in the MKLI medium, these preadipocytes can be differentiated into megakaryocytes/platelets. However, mesenchymal cells such as preadipocytes and mesenchymal cell-derived megakaryocytes produce TPO having a differentiation-inducing property to platelets have not yet been reported.

It has been also known that if preadipocytes are cultured in a culture medium containing dexamethasone, 3-isobutyl-1-methylxanthine, insulin and indomethacin, they are induced to differentiate into adipose cells (non-patent document 25). However, it has been believed that TPO is produced in the hepatocytes; and never known that TPO is produced during the process of differentiating preadipocytes into adipose cells.

Note that, in connection with cell-surface markers to be used in the present invention, the following facts are known. CD31 is expressed on e.g., vascular endothelial cells and involved in adhesion between cells. c-MPL protein (Myeloproliferative leukemia protein) is a receptor for thrombopoietin having differentiation/growth action of megakaryocytes producing platelets. c-MPL is expressed not only on platelets and megakaryocytes but also on erythroblasts. CD71 is a type II membrane glycoprotein and known as a transferrin receptor. CD71 is expressed not only on activated T cells and activated B cells but also on macrophages and all proliferating cells.

PRIOR ART DOCUMENTS

Non-Patent Documents

Non-patent document 1: Stroncek D F, Rebulla P. Platelet transfusions. Lancet. 2007; 370 (9585): 427-438.

Non-patent document 2: Freireich E J. Origins of platelet transfusion therapy. Transfus Med Rev. 2011; 25 (3): 252-256.

Non-patent document 3: Reems J A, Pineault N, Sun S. In vitro megakaryocyte production and platelet biogenesis: state of the art. Transfus Med Rev. 2010; 24 (1): 33-43.

Non-patent document 4: Gaur M, Kamata T, Wang S, et al. Megakaryocytes derived from human embryonic stem cells: a genetically tractable system to study megakaryocytopoiesis and integrin function. J Thromb Haemost. 2006; 4 (2): 436-442.

Non-patent document 5: Takayama N, Nishikii H, Usui J, et al. Generation of functional platelets from human embryonic stem cells in vitro via ES-sacs, VEGF-promoted structures that concentrate hematopoietic progenitors. Blood. 2008; 111 (11): 5298-5306.

Non-patent document 6: Takayama N, Nishimura S, Nakamura S, et al. Transient activation of c-MYC expression is critical for efficient platelet generation from human induced pluripotent stem cells. J Exp Med. 2010; 207 (13): 2817-2830.

Non-patent document 7: Nakamura S, Takayama N, Hirata S, et al. Expandable Megakaryocyte Cell Lines Enable Clinically Applicable Generation of Platelets from Human Induced Pluripotent Stem Cells. Cell Stem Cell. 2014 Feb. 12.pii: S1934-5909 (14)00012-5. doi: 10.1016/j.stem.2014.01.011.

Non-patent document 8: Ono Y, Wang Y, Suzuki H, et al. Induction of functional platelets from mouse and human fibroblasts by p45NF-E2/Maf. Blood. 2012; 120: 3812-3821.

Non-patent document 9: Matsubara Y, Murata M, Ikeda Y, Culture of megakaryocytes and platelets from subcutaneous adipose tissue and a preadipocyte cell line. Methods Mol Biol. 2012; 788: 249-258.

Non-patent document 10: Matsubara Y, Saito E, Suzuki H, Watanabe N, Murata M, et al. Generation of megakaryocytes/platelets from human subcutaneous adipose tissues. Biochem Biophys Res Commun. 2009; 378: 716-720.

Non-patent document 11: Matsubara Y, Suzuki H, Ikeda Y, Murata M. Generation of megakaryocytes/platelets from preadipocyte cell line 3T3-L1, but not the parent cell line 3T3, in vitro. Biochem Biophys Res Commun. 2010; 402: 796-800.

Non-patent document 12: Williams, N. et al. J Cell Physiol 1982; 110, 101-104.

Non-patent document 13: Teramura, M. et al. Exp Hematol 1988; 16, 843-848.

Non-patent document 14: Teramura, M. et al. Exp Hematol 1989; 17, 1011-1016.

Non-patent document 15: Teramura, M. & Mizoguchi, H. Int J Cell Cloning 1990; 8, 245-252.

Non-patent document 16: Teramura, M. et al. Blood 1992; 79, 327-331.

Non-patent document 17: Burstein, S. A. et al. Blood 1990; 76, 450a.

Non-patent document 18: de Sauvage, et al. Nature 1994; 369, 533-538.

Non-patent document 19: Kaushansky K. Thrombopoietin. N Engl J Med 1998; 339:746-754.

Non-patent document 20: Kuter D J, and Begley C G. Recombinant human thrombopoietin: basic biology and evaluation of clinical studies. Blood 2002; 100:3457-3469.

Non-patent document 21: Kappers-Klunne M C, de Haan M, Struijk P C et al. Serum thrombopoietin levels in relation to disease status in patients with immune thrombocytopenic purpura. Br J Haematol 2001; 115:1004-1006.

Non-patent document 22: Kuter D J. Future directions with platelet growth factors. Semin Hematol 2000; 37:41-49.

Non-patent document 23: Vadhan-Raj S, Verschraegen C F, Bueso-Ramos C et al. Recombinant human thrombopoietin attenuates carboplatin-induced severe thrombocytopenia and the need for platelet transfusions in patients with gynecologic cancer. Ann Intern Med 2000; 132:364-368.

Non-patent document 24: Vadhan-Raj S, Patel S, Bueso-Ramos C et al. Importance of predosing of recombinant human thrombopoietin to reduce chemotherapy-induced early thrombocytopenia. J Clin Oncol 2003; 21:3158-3167.

Non-patent document 25: Shandadfar A1, Fronsdal K, Haug T, Reinholt F P, Brinchmann J E. In vitro expansion of human mesenchymal stem cells: choice of serum is a determinant of cell proliferation, differentiation, gene expression, and transcriptome stability. Stem Cells. 2005: 1357-66.

SUMMARY OF THE INVENTION

Object to be Solved by the Invention

The object of a first invention is to provide a more practical megakaryocytes and/or platelets production method, enabling to produce megakaryocytes having platelet producibility and/or platelets having thrombus forming ability from mesenchymal cells such as preadipocytes in a relatively short period of time, simply and in a large amount as well as at lower cost or more efficiently in vitro. Other objects according to second and third inventions are to provide a method for producing TPO having an ability to induce/promote platelet production easily and in a large amount, and a method for producing practical TPO having fewer side effects.

Means to Solve the Object

First, means to attain the object of a first invention will be described below. It has been considered that TPO is essential for inducing differentiation of preadipocytes into megakaryocytes/platelets, similarly to inducing differentiation of hematopoietic stem cells into megakaryocytes/platelets. In the context, the present inventors cultured preadipocytes in a medium prepared by removing TPO from MKLI medium, which is known as differentiation-inducing medium into megakaryocytes/platelets. As a result, they found, against expectation, that differentiation of megakaryocytes/platelets is induced. The present inventors have further conducted studies. They prepared a medium (one of the basic mediums for culturing mesenchymal cells used in the present invention) by removing six components, namely, TPO, bovine serum albumin (BSA), LDL-cholesterol, iron-bound transferrin, insulin and 2-β-mercaptoethanol, from MKLI medium, and prepared five mediums by adding the five components excluding TPO one by one, and then, preadipocytes were cultured in these five mediums. As a result, the present inventors found that megakaryocytes and platelets are produced only in a medium prepared by adding iron-bound transferrin to the basic medium.

The present inventors knocked down a transferrin receptor, CD71 by siRNA. As a result, they found that the ratio (%) of CD41 (specific marker of megakaryocytes/platelets)-positive cells decreases, and production of megakaryocytes and platelets is suppressed. The present inventors further prepared mediums ("basic medium+iron-bound transferrin") by removing TPO, BSA, LDL cholesterol, insulin and 2-β-mercaptoethanol from MKLI medium and adding iron-bound transferrin in different concentrations and investigated on production of megakaryocytes and platelets from preadipocytes in these mediums. As a result, they found that even if the concentration of iron-bound transferrin is lower than that (200 µg/mL) in a conventional MKLI medium, almost the same level of megakaryocytes and platelets can be produced as in the case of 200 µg/mL. In addition, the present inventors prepared a medium by adding an iron chelator or apo-transferrin (transferrin not bound to iron) to the basic medium containing iron-bound transferrin and cultured preadipocytes in the medium. As a result, they found that the number of megakaryocytes and platelets decreases in a dose dependent manner of the iron chelator and apo-transferrin. The present inventors compared preadipocyte-derived platelets and hematopoietic stem cell-derived platelets for thrombus forming ability. As a result, they found that the preadipocyte-derived platelets have significantly increased percentage of platelets contributing to thrombus formation compared with hematopoietic stem cell-derived platelets.

From these results, the present inventors found that an iron ion and an iron transporter are extremely important to produce megakaryocytes and platelets from mesenchymal cells such as preadipocytes, and particularly at least an iron ion is essential.

The present inventors further conducted studies on a method for more efficiently producing megakaryocytes and platelets from mesenchymal cells such as preadipocytes. As a result, they found that in particular, mesenchymal cells having a predetermined cell-surface marker profile, namely, CD31 negative and CD71 positive mesenchymal cells, preferably mesenchymal cells further positive to c-MPL can be differentiated into megakaryocytes and platelets with higher efficiency.

From the findings mentioned above, the present inventors have achieved the first invention.

Next, means to attain the object of a second invention will be described below. It has been considered that TPO is essential in differentiation induction of preadipocytes into megakaryocytes/platelets, similarly to differentiation induction of hematopoietic stem cells into megakaryocytes/platelets. In the context, the present inventors prepared a medium ("MKLI medium-TPO") by removing TPO from MKLI medium, known as megakaryocyte/platelet differentiation induction medium, cultured preadipocytes to obtain a culture, and then cultured hematopoietic stem cells in the culture supernatant of the culture. As a result, they found, against expectation, that differentiation induction into megakaryocytes/platelets occurs. The present inventors investigated the presence or absence of TPO in the culture supernatant of a culture obtained by culturing preadipocytes in the "MKLI medium-TPO". As a result, they found that TPO is present in the culture supernatant in a relatively high concentration. The present inventors knocked down, a receptor of transferrin, i.e., CD71, by siRNA. As a result, they found that TPO production is suppressed by knock down of CD71. The present inventors prepared a medium ("basic medium+transferrin") by removing TPO, bovine serum albumin (BSA), LDL cholesterol, insulin and 2-β-mercaptoethanol from MKLI medium and adding iron-bound transferrin and a medium ("MKLI medium-TPO") by removing TPO from MKLI medium, and investigated a change of TPO concentration when preadipocytes were cultured. As a result, TPO can be consistently produced when "basic medium+transferrin" is used. The present inventors further investigated TPO production from preadipocytes by changing the concentration of iron-bound transferrin in "basic medium+transferrin". As a result, they found that even if the concentration of iron-bound transferrin is lower than that (200 µg/mL) in a conventional MKLI medium, TPO can be produced at a level almost equal to or larger than the concentration of 200 µg/mL. In addition, the present inventors investigated expression of TPO mRNA in preadipocytes in a primary culture and established mesenchymal stem cells, stromal cells and preadipocytes. As a result, they found that TPO mRNA is expressed in any one of these cells.

From the findings mentioned above, the present inventors have achieved the second invention.

Next, means to attain the object of a third invention will be described below. It is known that when preadipocytes are cultured in a culture medium containing dexamethasone, 3-isobutyl-1-methylxanthine and insulin, they are induced to differentiate into adipose cells. However, it was believed that TPO is produced in the hepatocytes and not known that TPO is produced during the differentiation process of preadipocytes into adipose cells. The present inventors coincidentally found, during detailed studies on the first and second inventions, that TPO is produced not only in differentiation induction of preadipocytes into megakaryocytes and platelets but also in differentiation induction of preadipocytes into adipose cells. This is a fact beyond expectation to those skilled in the art.

From the findings mentioned above, the present inventors have achieved the third invention.

More specifically, the present invention consists of, (1) A method for producing a megakaryocyte and/or platelet, comprising culturing a mesenchymal cell in a mesenchymal cell culturing basic medium containing an iron ion and an iron transporter and collecting the megakaryocyte and/or platelet from a culture;

(2) A method for producing thrombopoietin, comprising culturing a mesenchymal cell or mesenchymal cell-derived megakaryocyte in a mesenchymal cell culturing basic medium containing an iron ion and an iron transporter and collecting thrombopoietin from a culture;

(3) The production method according to (1) or (2) above, wherein the mesenchymal cell is a CD31 negative and CD71 positive mesenchymal cell;

(4) The production method according to any one of (1) to (3) above, wherein the CD31 negative and CD71 positive mesenchymal cell is further positive to c-MPL;

(5) The production method according to any one of (1) to (4) above, wherein the iron transporter is transferrin;

(6) The production method according to any one of (1) to (5) above, wherein the iron ion and iron transporter are an iron-bound transferrin;

(7) The production method according to any one of (1) and (3) to (6) above, wherein the culturing is performed for 5 to 17 days;

(8) The production method according to any one of (2) to (6) above, wherein the culturing is performed for 4 to 7 days;

(9) The production method according to any one of (1) and (3) to (7) above, wherein the yield of the megakaryocyte and/or platelet is 270 to 1,080%;

(10) The production method according to any one of (1), (3) to (7) and (9) above, wherein a percentage of platelets contributing to thrombus formation as measured by thrombus formation analysis of the platelets is 70% to 85%;

(11) The production method according to any one of (2) to (6) and (8) above, wherein the yield of TPO per 1 mL of medium is 30 pg to 100 pg;

(12) The production method according to any one of (1), (3) to (7), (9) and (10) above, further comprising a step of purifying the megakaryocyte and/or platelet from the culture; and

(13) The production method according to any one of (2) to (6), (8) and (11) above, further comprising a step of purifying TPO from the culture.

The present invention further consists of

(14) A megakaryocyte and/or platelet produced by the production method according to any one of (1), (3) to (7), (9), (10) and (12) above; and

(15) A TPO produced by the production method according to any one of (2) to (6), (8), (11) and (13) above.

The present invention further consists of

(16) A method for constructing a megakaryocyte and/or platelet bank, comprising the following steps a) to c):

a) providing various types of mesenchymal cells of different HLA types and/or HPA types;

b) selecting a specific HLA type and/or HPA type of mesenchymal cell among the mesenchymal cells provided in the step a); and c) preparing the specific HLA type and/or HPA type of megakaryocyte and/or platelet using the mesenchymal cells selected in the step b) by the production method according to any one of (1), (3) to (7), (9), (10), (12) and (14) above.

The present invention further consists of,

(17) A method for producing thrombopoietin, comprising culturing a preadipocyte in a preadipocyte culturing basic medium containing an agent for inducing differentiation to a mature adipocyte, and collecting thrombopoietin from a culture; and

(18) The method for producing thrombopoietin according to (17) above, wherein the agent for inducing differentiation into a mature adipocyte is one or more selected from the group consisting of 3-isobutyl-1-methylxanthine, insulin, dexamethasone and indomethacin.

Effect of the Invention

According to the first invention, it is possible to provide a method for producing more practical megakaryocytes and/or platelets enabling to produce megakaryocytes having platelet producibility and/or platelets having thrombus forming ability from mesenchymal cells such as preadipocytes in a relatively short period of time, simply and in a large amount as well as at lower cost or more efficiently in vitro. If mesenchymal cells derived from a subject, to which megakaryocytes and platelets are to be administered, are used as the mesenchymal cells to be used in the first invention, megakaryocytes and platelets having the identical HLA type and HPA type to those of the administration subject can be produced. Such megakaryocytes and platelets are very excellent even if they are administered to a subject, antibodies that cross-react with e.g., endogenous megakaryocytes and platelets are not induced and a refractory state will not occur even if they are frequently transfused. In addition, if mesenchymal cells having a predetermined cell-surface marker profile, more specifically, CD31 negative and CD71 positive mesenchymal cells, preferably, mesenchymal cells further positive to c-MPL, are used as the mesenchymal cells to be used in the first invention, they can be differentiated into megakaryocytes and platelets with higher efficiency.

According to the second and third inventions, it is possible to provide a method for producing TPO having an ability to induce/promote platelet production, easily and in a large amount. Furthermore, if mesenchymal cells and mesenchymal cell-derived megakaryocytes derived from a subject, to which TPO is to be administered, are used as the mesenchymal cells and mesenchymal cell-derived megakaryocytes to be used in the second invention, or if preadipocytes derived from a subject, to which TPO is to be administered, are used as the preadipocytes to be used in the third invention, practical TPO having fewer side effects can be manufactured.

BRIEF DESCRIPTION OF DRAWINGS

FIG. 1 shows production of megakaryocytes/platelets from mesenchymal cells. [FIG. 1, upper-stage panels] The panels show the culture results of mouse stromal cells (OP9 cells) in MKLI medium. The left panel shows the results immediately after initiation of culture for differentiation induction; the center panel shows the results on Day 7; and the right panel shows the results on Day 10 after initiation of culture for differentiation induction. [FIG. 1, lower-stage panels] The panels show the culture results of human preadipocytes (HPAd cell) in MKLI medium. The left panel shows the results immediately after initiation of culture for differentiation induction; the center panel shows the results on Day 7; and the right panel shows the results on Day 10 after initiation of culture for differentiation induction.

FIG. 2 is a graph showing the analysis results of the cells obtained by culturing human preadipocytes in MKLI medium. [FIG. 2, left panel] The panel shows the measurement results of fluorescence of PI by flow cytometry, when the cells obtained by culturing human preadipocytes in MKLI medium were stained with propidium iodide (PI). [FIG. 2, right panel] The panel shows the measurement results of fluorescence from the antibody labels attached to CD41 and CD42b, which are specific markers of megakaryocytes and platelets, of the cells obtained by culturing human preadipocytes in MKLI medium.

FIG. 3 is a schematic illustration how to analyze thrombus forming ability.

FIG. 4 shows the analysis results of thrombus forming ability. [FIG. 4, upper-stage panels] The panels show the chip portions of a thrombus formation analysis system, to which a blood sample taken from a thrombocytopenia mouse transfused with megakaryocytes produced from preadipocytes was refluxed. The left panel shows a general micrograph; whereas the right panel shows a photograph in which fluorescence from a label attached to megakaryocytes was detected. [FIG. 4, lower-stage left panels] The panels show the chip portions of the thrombus formation analysis system before a blood sample was refluxed. [FIG. 4, lower-stage right panel] The panel shows the chip portions of the thrombus formation analysis system, to which a blood sample taken from a thrombocytopenia mouse not transfused with megakaryocytes was refluxed.

FIG. 5 illustrates details of mediums used in the experiment of Example 3 and the results showing whether megakaryocytes/platelets were produced or not by culture using these mediums.

FIG. 6 is a graph showing the measurement results on the effect of anti-c-MPL antibody (AMM2 antibody), which is a c-MPL neutralizing antibody, upon production of megakaryocytes/platelets from preadipocytes. The horizontal axis shows the concentration (µg/mL) of AMM2 antibody; whereas the vertical axis shows the number of CD41 positive cells.

FIG. 7 shows the flow cytometric measurement results of fluorescence emitted from markers attached to adipose tissue-derived cells. [FIG. 7, upper left panel] The panel shows the measurement results of fluorescence emitted from adipose tissue-derived cells. [FIG. 7 upper right panel] The panel shows the measurement results of fluorescence emitted from a fluorescence-labeled anti-CD45 antibody, a fluorescence-labeled anti-Ter119 antibody and 7-AAD attached to adipose tissue-derived cells. [FIG. 7, lower left panel] The panel shows the measurement results of fluorescence emitted from a fluorescence-labeled anti-CD31 antibody, which is attached to CD45 negative, Ter119 negative and 7-AAD negative cells separated from the cells shown in the upper right panel of FIG. 7. [FIG. 7, lower right panel] The panel shows the measurement results of fluorescence emitted from a fluorescence-labeled anti-c-MPL antibody and a fluorescence-labeled anti-CD71 antibody attached to CD31 negative cells separated from the cells shown in the lower left panel of FIG. 4.

FIG. 8 shows the ratio (%) of CD41 positive cells obtained by culturing the cells shown in the portions of FIG. 7, lower right panel (FIG. 8, left panel) in the basic medium supplemented with an iron-bound transferrin for 5 days. [FIG. 8, lower right panel] The panel shows detection results and the ratio (10.8%) of CD41 positive cells when the cells (CD45 negative, Ter119 negative, CD31 negative, c-MPL negative and CD71 negative cells) shown in the lower left portion of FIG. 8, left panel were cultured. [FIG. 8, right center panel] The panel shows detection results and the ratio (26.9%) of CD41 positive cells when the cells (CD45 negative, Ter119 negative, CD31 negative, c-MPL negative and CD71 positive cells) shown in the lower right portion of FIG. 8, left panel were cultured. [FIG. 8, upper right panel] The panel shows detection results and the ratio (62.3%) of CD41 positive cells when the cells (CD45 negative, Ter119 negative, CD31 negative, c-MPL positive and CD71 positive cells) shown in the upper right portion of FIG. 8, left panel were cultured.

FIG. 9 shows the activity of TPO produced from preadipocytes for producing megakaryocytes and platelet. [FIG. 9, upper-stage panels] The panels show culture results of hematopoietic stem cells in the culture supernatant taken from a culture of preadipocytes in "MKLI medium-TPO". The left panel shows the results on Day 2 after initiation of culture; whereas the right panel shows the results on Day 8. [FIG. 9, middle-stage panels] The panels show the culture results of hematopoietic stem cells in MKLI medium containing TPO. The left panel shows the results on Day 2 after initiation of culture; whereas the right panel shows the results on Day 8. [FIG. 9, lower-stage panels] The panels show the culture results of hematopoietic stem cells in "MKLI medium-TPO" not containing TPO. The left panel shows the results on Day 2 after initiation of culture; whereas the right panel shows the results on Day 8.

MODE OF CARRYING OUT THE INVENTION

[First Invention]

A method for producing megakaryocytes and/or platelets according to the first invention (hereinafter referred to simply as "the production method of the first invention") is not particularly limited as long as it is a method including culturing mesenchymal cells in a mesenchymal cell culturing basic medium containing an iron ion and an iron transporter (hereinafter referred to as "the culture medium to be used in the first invention") and collecting megakaryocytes and/or platelets from a culture. The "medium" herein refers to a state of medium obtained by adding water to "medium components" capable of culturing cells. Although it is not specifically clarified which mechanism of action underlies in producing megakaryocytes and platelets by culturing mesenchymal cells such as preadipocytes in the mesenchymal cell culturing basic medium containing an iron ion and an iron transporter, it is considered that an iron ion taken in mesenchymal cells or an iron ion and iron transporter promote TPO secretion from the cells by unknown mechanism, contributing to acceleration of differentiation induction of the cells into megakaryocytes/platelets. Note that it is known that separation membrane is formed in megakaryocytes when they are matured, and segments the cytoplasm of the megakaryocytes to produce platelets. It is reported that 2,000 to 7,000 of platelets are released from a single megakaryocyte.

The mesenchymal cells to be used in the first invention are not particularly limited as long as mesenchymal cells can produce megakaryocytes and platelets by culturing them in the mesenchymal cell culturing basic medium containing an iron ion and an iron transporter. As the mesenchymal cells, (a) preadipocytes (adipose progenitor cells), (b) mesenchymal stem cells and (c) stromal cells can be mentioned. As the mesenchymal stem cells, subcutaneous adipose tissue-derived mesenchymal stem cells and bone marrow mesenchymal stem cells can be mentioned. As the stromal cells, adipose tissue-derived stromal cells, bone marrow stromal cells, prostate-derived stromal cells and endometrial-derived stromal cells can be mentioned. As the preferable mesenchymal cells, preadipocytes and subcutaneous adipose tissue-derived mesenchymal stem cells can be mentioned. The mesenchymal cells to be used in the first invention can be a cell line or cells (including primary cultured cells and subcultured cells) taken from a tissue. As specific examples of the mesenchymal cells to be used in the first invention, human primary-culture preadipocytes (HPAd cell), mouse primary-culture progenitor cells (subcutaneous adipose tissue-derived), established mouse stromal cells (OP9 cells), established mouse bone marrow mesenchymal stem cells (HS-22 cells) and established mouse preadipocytes (3T3-L1 cells) can be mentioned. Note that as long as the effects of the first invention (megakaryocytes having platelet producibility and/or platelets having thrombus forming ability can be simply produced in a relatively short period of time, in a large amount, at lower cost and more efficiently in vitro) can be obtained, the production method of the first invention can be applied to stem cells other than mesenchymal cells.

As a cell line of the above mesenchymal cells and mesenchymal cells taken from a tissue, cells commercially available from companies such as Lonza, PromoCell, CELL APPLICATIONS and the JCRB cell bank of the National Institute of Biomedical Innovation can be used; however, the mesenchymal cells taken from a tissue of a subject, to which megakaryocytes and platelets obtained by the production method of the first invention are to be administered, are preferably used, because if such mesenchymal cells are used, the HLA type and HPA type of megakaryocytes and platelets coincide with those of the subject to be administered, with the result that when the megakaryocytes and platelets are administered to the subject, endogenous antibodies that cross-react with the megakaryocytes and platelets are not induced and a refractory state is not resulted even if transfusion is frequently repeated.

In the case where a cell line is used as mesenchymal cells, mesenchymal cells can be prepared and established, and then put in use. The method for establishing mesenchymal cells is not particularly limited and e.g., a known method can be used. As a preferable method for establishing preadipocytes, a method as described in Example 15 can be mentioned, in which preadipocytes are induced to differentiate into mature adipocytes, which are subjected to a ceiling culture method known as a method for establishing mature adipocytes to obtain established preadipocytes. If the mesenchymal cells are established, differentiation potency and proliferation potency are semi-permanently maintained. Thus, if the mesenchymal cell line is e.g., cryopreserved, production of megakaryocytes and platelets can be advantageously started immediately at the time of need.

In order to more efficiently produce megakaryocytes and platelets, the mesenchymal cells to be used in the first invention are preferably CD31 negative and CD71 positive mesenchymal cells (preferably preadipocytes), and more preferably CD31 negative, CD71 positive and c-MPL positive mesenchymal cells (preferably preadipocytes). As described above, in the case where preadipocytes are established, CD31 negative, CD71 positive and c-MPL positive preadipocytes are previously selected from preadipocytes and subjected to the aforementioned cell establishment method.

The preadipocytes and subcutaneous adipose tissue-derived mesenchymal stem cells can be taken from a subcutaneous adipose tissue and an adipose tissue such as a visceral tissue (fat); the bone marrow mesenchymal stem cells can be taken from a myeloid tissue; and stromal cells can be taken from e.g., an adipose tissue, a bone marrow tissue, the prostate and the endometrium. As the aforementioned preadipocytes and subcutaneous adipose tissue-derived mesenchymal stem cells, mesenchymal cells derived from an adipose tissue (preferably subcutaneous adipose tissue) can be preferably mentioned because sampling can be made by a less invasive manner and a larger number of mesenchymal cells can be more simply taken. As a method for taking mesenchymal cells from a tissue, an ordinary method can be used.

Mesenchymal cells having a predetermined cell-surface marker profile such as CD31 negative and CD71 positive mesenchymal cells, or CD31 negative, CD71 positive and c-MPL positive mesenchymal cells can be screened based on the presence or absence of their specific cell-surface markers used as indexes from a cell population including mesenchymal cells. In the first invention, screening of mesenchymal cells having a predetermined cell-surface marker profile include isolating only mesenchymal cells having a predetermined cell-surface marker profile from a cell population including mesenchymal cells such that the ratio of mesenchymal cells having a predetermined cell-surface marker profile increases from that of the cell population before screening.

A method for screening the mesenchymal cells having a predetermined cell-surface marker profile is not particularly limited. In order to more easily and quickly screen desired mesenchymal cells, for example, a method for screening mesenchymal cells having a predetermined cell-surface marker profile by using an antibody (preferably a labeled antibody, more preferably a fluorescence-labeled antibody) against each of the cell-surface markers mentioned above and based on the presence or absence of specific binding of each of the antibodies used as an index, can be suitably mentioned. The above phrase: "screened based on the presence or absence of specific binding of each of the antibodies used as an index" refers to screening cells in which the antibody against a cell-surface marker indicated as "positive" in the profile shows specific binding to the marker and screening cells in which the antibody against a cell-surface marker indicated as "negative" in the profile does not show specific binding (to the marker). To describe this more specifically, in the case where CD31 negative and CD71 positive mesenchymal cells are screened from a mesenchymal cell population, the phrase means that the cells showing no specific binding to an anti-CD31 antibody and showing specific binding to an anti-CD71 antibody are screened. The method of screening mesenchymal cells having a predetermined cell-surface marker profile based on the presence or absence of specific binding of an antibody used as an index is not particularly limited; however, a method of using e.g., a cell sorter, magnetic beads or a cell adsorption column can be mentioned. Because it is a more convenient and quick method, a method of using a cell sorter can be preferably mentioned. The method using a cell sorter is based on flow cytometry and well known to those skilled in the art. Specific methods are described in not only the instruction booklet of a cell sorter but also e.g., Japanese Unexamined Patent Application Publication (Translation of PCT Application) No. 2009-513161. The method using magnetic beads is well known to those skilled in the art as e.g., a magnetic separation method. As a specific method, a separation method by bringing magnetic beads carrying a predetermined antibody into contact with cells and collecting magnetic beads by a magnet, thereby separating cells specifically binding to the predetermined antibody can be mentioned. Furthermore, the method using a cell adsorption column is well known to those skilled in the art. As a specific method, an adsorption method by bringing cells into contact with a cell adsorption column carrying a predetermined antibody and allowing the cells except desired cells to adsorb to the column can be mentioned.

In taking CD31 negative and CD71 positive mesenchymal cells (preferably preadipocytes) and CD31 negative, CD71 positive and c-MPL positive mesenchymal cells (preferably preadipocytes) from an adipose tissue, it is preferable to use "being CD45 (marker of hematopoietic cells except erythrocytes and platelets)-negative and Ter119 (marker of erythrocytes and progenitor cells thereof)-negative" as indexes in addition to these cell-surface markers, because blood-associated cells contained in the adipose tissue can be eliminated. Since CD45 and Ter119 are not expressed on the surface of mesenchymal cells, if cells are mesenchymal cells, it is not necessary to check whether the cells are CD45 and Ter119 negative or not. In addition, although it is not a cell-surface marker, "being 7-amino-actinomycin D (7-AAD) negative" is preferably used as an index, because dead cells contained in the adipose tissue can be eliminated. 7-AAD intercalates in the DNA chains of dead cells and emits red fluorescence by irradiation of excitation light of 488 nm.

As a fluorescence-labeled anti-CD45 antibody, a fluorescence-labeled anti-Ter119 antibody, a fluorescence-labeled anti-CD31 antibody, a fluorescence-labeled anti-c-MPL antibody and a fluorescence-labeled anti-CD71 antibody, the fluorescence-labeled antibodies commercially available from e.g., Immuno-Biological Laboratories Co., Ltd., and BD Biosciences can be used. As 7AAD, products commercially available from e.g., BD Biosciences can be used.

In the production method of the first invention, if CD31 negative and CD71 positive mesenchymal cells, preferably mesenchymal cells further positive to c-MPL are used, it is preferable that the production method further includes screening CD31 negative and CD71 positive mesenchymal cells (preferably preadipocytes), preferably, mesenchymal cells further positive to c-MPL (preferably preadipocytes) from a cell population including mesenchymal cells, before the mesenchymal cells are cultured in the mesenchymal cell culturing basic medium containing an iron ion and an iron transporter. If a cell population derived from an adipose tissue is used as the cell population including mesenchymal cells, it is preferable that a cell-surface marker profile: CD45 negative and Ter119 negative is used as an index in addition to a cell-surface marker profile: CD31 negative, CD71 positive, preferably further positive to c-MPL, because blood-associated cells except mesenchymal cells can be efficiently eliminated. It is further preferable to confirm that the cells are 7-AAD negative because dead cells contained in the adipose tissue can be efficiency eliminated.

An organism species, from which the mesenchymal cells are derived, is not particularly limited as long as it is a vertebrate. As the vertebrate, a mammal, a bird, a reptile, an amphibian and fish can be mentioned. Of them, mammals such as a human, a mouse, a rat, a guinea pig, a rabbit, a cat, a dog, a horse, a cow, a monkey, a sheep, a goat and a pig can be preferably mentioned. Of them, a human can be particularly preferably mentioned.

The culture medium to be used in the first invention is a medium prepared by adding an iron ion and an iron transporter to the mesenchymal cell culturing basic medium.

As the iron ion, either an iron ion (II) or an iron ion (III) can be used; however, an iron ion (III) can be preferably mentioned. As a method for adding an iron ion to the mesenchymal cell culturing basic medium, a method of adding one or more salts of an iron selected from the group consisting of inorganic salts and organic salts of iron to the mesenchymal cell culturing basic medium can be mentioned. As such a salt of iron, an inorganic salts or an organic salt can be used. Examples of the inorganic salt can include iron (II) chloride, iron (III) chloride, iron (II) oxide, iron (III) oxide, iron (II) nitrate, iron (III) nitrate, iron (II) sulfate, iron (III) sulfate, ammonium iron (II) sulfate, ammonium (III) iron sulfate, iron (II) pyrophosphate, iron (III) pyrophosphate, iron (II) sulfide, iron (III) sulfide, iron (II) hydroxide and iron (III) hydroxide oxide. Examples of the organic salt can include iron (II) acetate, iron (III) acetate, iron (III) hydroxide diacetate, iron (II) citrate, iron (III) citrate, sodium iron (III) citrate, ammonium iron (III) citrate, iron (II) benzoate, iron (III) benzoate, iron (II) carbonate, iron (III) carbonate, iron (II) formate, iron (III) formate, iron (II) oxalate, iron (III) oxalate, iron (II) fumarate, iron (III) fumarate, iron (II) succinate, iron (III) succinic, iron (II) gluconate, iron (III) gluconate, iron (II) lactate, iron (III) lactate, iron (II) maleate, iron (III) maleate, sodium iron (III) diethylenetriaminepentaacetate, ammonium iron (III) diethylenetriaminepentaacetate, sodium iron (III) ethylenediaminetetraacetate, ammonium iron (III) ethylenediaminetetraacetate, sodium iron (III) dicarboxymethylglutamate and ammonium iron (III) dicarboxymethyl-glutamate. These salts of iron can be used alone or in combination of two or more. As these salts of iron, commercially available ones can be used.

The iron transporter binds to an iron ion contained in a culture medium to be used in the first invention and allows mesenchymal cells to take an iron ion from the culture medium. If an iron transporter bound to an iron ion is used, it functions also as an iron supply source. The iron transporter not bound to iron is called as "apo" type; whereas the ion transporter bound to iron is called as "holo" type. The iron transporter bound to a middle level of iron between the apo-type and the holo-type is sometimes called as "sidero" type. As the iron transporter, proteins that can bind to iron and can be incorporated into cells (e.g., Japanese Unexamined Patent Application Publication No. H08-029429, Japanese Unexamined Patent Application Publication (Translation of PCT Application) Nos. 2005-517042, 2004-505932 and 2007-508026) can be mentioned. Examples of the apo-type iron transporter or corresponding thereto include apo-transferrin (apo-serotransferrin), apo-lactoferrin, apo-ovotransferrin, apo-melanotransferrin, apo-ferritin and protoporphyrin IX. Of them, apo-transferrin can be preferably mentioned. As an organism species, from which such an iron transporter is derived, an allogenic organism species, from which mesenchymal cells that are to be used together are derived, is preferably used.

As the iron ion and iron transporter in the first invention, a complex (iron ion-iron transporter complex), which is formed by binding an iron ion and an iron transporter, can be preferably used. Examples of such an iron ion-iron transporter complex can include, a holo-transferrin (iron-bound transferrin) formed by binding an apo-transferrin to an iron ion, a holo-lactoferrin (iron-bound lactoferrin) formed by binding apo-lactoferrin to an iron ion, a holo-ovotransferrin (iron-bound ovotransferrin) formed by binding apo-ovotransferrin to an iron ion, a holo-melanotransferrin (iron-bound melanotransferrin) formed by binding an apo-melanotransferrin to an iron ion, a holo-ferritin (iron-bound ferritin) formed by binding apo-ferritin to an iron ion and heme formed by binding protoporphyrin IX to iron. Of them, an iron-bound transferrin can be particularly preferably mentioned. As the holo-type iron transporter bound to an iron ion, apo-type iron transporter not bound to an iron ion and a sidero-type iron transporter, which is bound to a middle level of ion between the apo-type and the holo, commercially available ones can be used.

The binding form of an iron ion and an iron transporter in the iron ion-iron transporter complex is not particularly limited and a noncovalent bond such as a coordinate bond, an ionic bond, a hydrogen bond, a metallic bond and van der Waals force, or a covalent bond can be acceptable; however, a coordinate bond can be preferably mentioned since it provides appropriately binding and it is suitable for transporting an iron ion into mesenchymal cells. Note that an iron ion-iron transporter complex, in which iron is not present in the state of ion, but capable of releasing an iron ion when the complex is taken into mesenchymal cells, is also included in the iron ion-iron transporter complex of the first invention, for convenience sake.

The concentration of iron ion in the culture medium to be used in the first invention is not particularly limited as long as platelets can be produced by culturing mesenchymal cells in the culture medium to be used in the first invention containing iron in the concentration. For example, the concentration within the range of 1 pg/mL to 10 μg/mL, preferably within the range of 10 pg to 1 μg/mL, more preferably within the range of 150 pg/mL to 300 pg/mL, and further preferably within the range of 150 pg/mL to 250 pg/mL can be mentioned.

The content of the iron transporter in the culture medium to be used in the first invention is not particularly limited as long as megakaryocytes and platelets can be produced by culturing mesenchymal cells in the culture medium to be used in the first invention having the content of the iron transporter. For example, a concentration within the range of 10 fM ($1 \times 10^{-15}$M) to 100 nM, preferably within the range of 100 fM to 10 nM, more preferably within the range of 1 pM to 2.8 pM and further preferably within the range of 1 pM to 2.5 pM can be mentioned.

When iron-bound transferrin is used in the culture medium to be used in the first invention, the concentration of the transferrin to be added is not particularly limited and can follow the numerical range of iron ion concentration. For example, a concentration of 25 μg/mL to less than 200 μg/mL and preferably 50 μg/mL to less than 200 μg/mL can be mentioned. Note that, it is known that about 1.3 μg of an iron ion is bound to 1 mg of iron bound transferrin.

The mesenchymal cell culturing basic medium to be used in the first invention is not particularly limited as long as megakaryocytes and platelets can be produced by culturing mesenchymal cells in the medium supplemented with an iron ion and an iron transporter of the first invention. A chemically synthesized medium is preferable because the medium is easily prepared and variation from lot to lot is prevented. The chemically synthesized medium preferably contains one or more types of sugars, one or more types of inorganic salts, one or more types of amino acids, and one or more types of vitamins and one or more types of other components.

Examples of the sugars can include monosaccharides such as glucose, lactose, mannose, fructose and galactose; and disaccharides such as sucrose, maltose and lactose. Of them glucose is particularly preferable. These sugars can be added alone or in combination of two or more.

Examples of the inorganic salts can include calcium chloride, calcium nitrate, copper sulfate pentahydrate, iron (III) nitrate nonahydrate, iron (II) sulfate heptahydrate, magnesium chloride hexahydrate, magnesium sulfate, potassium chloride, sodium chloride, sodium hydrogen carbonate, disodium hydrogen phosphate, disodium hydrogen phosphate dihydrate, sodium dihydrogen phosphate, sodium dihydrogen phosphate monohydrate, sodium dihydrogen phosphate dihydrate, sodium selenite pentahydrate and zinc sulfate heptahydrate. These inorganic salts can be used alone or in combination of two or more. Any one or combination of inorganic salts can be used as long as they are components advantageously functioning for producing megakaryocytes and platelets from mesenchymal cells.

As the amino acid(s), one or more amino acids selected from e.g., alanine, arginine, asparagine, aspartic acid, cystine, cysteine, glutamine, glycine, histidine, glutamic acid, hydroxyproline, isoleucine, leucine, lysine, methionine, phenylalanine, proline, serine, threonine, tryptophan, tyrosine and valine, and preferably L-form amino acids and those derived from the L-form amino acids such as derivatives, salts and hydrates thereof can be specifically mentioned. As arginine, for example, an arginine derivative such as L-arginine hydrochloride and L-arginine monohydrochloride can be mentioned. As aspartic acid, aspartic acid derivatives such as sodium L-aspartate monohydrate, L-aspartic acid monohydrate, potassium L-aspartate and magnesium L-aspartate can be mentioned. As cysteine, cysteine derivatives such as L-cystine dihydrochloride and L-cysteine hydrochloride monohydrate can be mentioned. As lysine, lysine derivatives such as L-lysine hydrochlorides can be mentioned. As glutamic acid, a glutamine derivative such as sodium L-glutamate can be mentioned. As asparagine, an asparagine derivative such as L-asparagine monohydrate can be mentioned. As tyrosine, tyrosine derivatives such as L-tyrosine disodium dihydrate can be mentioned. As histidine, histidine derivatives such as histidine hydrochloride and histidine hydrochloride monohydrate can be mentioned. As lysine, lysine derivatives such as L-lysine hydrochloride can be mentioned.

As the vitamins, one or more vitamins selected from e.g., biotin, choline, folic acid, inositol, niacin, pantothenic acid, pyridoxine, riboflavin, thiamine, vitamin B12, para-aminobenzoic acid (PABA), ascorbic acid, and those derived from these vitamins, such as derivatives, salts and hydrates thereof, can be specifically mentioned. For example, as choline, choline derivatives such as choline chloride can be mentioned. As niacin, niacin derivatives such as nicotinic acid, nicotinic acid amide and nicotinic alcohol, can be mentioned. As pantothenic acid, pantothenic acid derivatives such as calcium pantothenate, sodium pantothenate and panthenol, can be mentioned. As pyridoxine, pyridoxine derivatives such as pyridoxine hydrochloride, pyridoxal hydrochloride, pyridoxal phosphate and pyridoxamine, can be mentioned. As thiamine, thiamine derivatives such as thiamine hydrochloride, thiamin nitrate, bisthiamine nitrate, thiamine dicetyl sulfate, fursultiamine hydrochloride, octotiamine and benfotiamine, can be mentioned. As ascorbic acid, ascorbic acid derivatives such as ascorbic acid 2-phosphate, ascorbic acid magnesium phosphate, ascorbic acid sodium sulfate, aminopropyl ascorbyl phosphate and sodium ascorbyl phosphate, can be mentioned.

As the other components, a buffering agent such as HEPES, a nucleic acid such as a nucleotide, an antibiotic such as penicillin and streptomycin, and pyruvic acid, and those derived from these substances, such as derivatives, salts and hydrates thereof, and phenol red can be mentioned. As the nucleotides, ATP, UTP, GTP and CTP, and preferably an equimolar mixture thereof can be mentioned. As the derivatives of the aforementioned antibiotics, sodium penicillin G and streptomycin sulfate or a penicillin-streptomycin solution can be preferably mentioned. As the pyruvic acid derivative, sodium pyruvate can be preferably mentioned.

As specific examples of the mesenchymal cell culturing basic medium, a chemically synthesized medium known in the art, such as commercially available Iscove's Modified Dulbecco's Medium (IMDM), RPMI 1640 medium, Dulbecco's modified Eagle's medium (DMEM), minimum essential medium (MEM), Eagle's basal medium (BME) and F12 medium; medium mixtures prepared by mixing two or more of these mediums in an appropriate ratio, such as a DMEM/F12 medium (DMEM and F12 mediums are mixed in a ratio of 1:1); and mediums prepared by further adding a nucleic acid such as a nucleotide, an antibiotic such as penicillin and streptomycin and L-glutamine to any one of these mediums, can be preferably mentioned. In particular, mediums prepared by further adding a nucleic acid (preferably, e.g., an equimolar mixture of ATP, UTP, GTP and CTP), an antibiotic (preferably, sodium penicillin G, streptomycin sulfate or a penicillin-streptomycin solution) and L-glutamine to IMDM and RPMI 1640 medium, can be preferably mentioned. Of them, a medium prepared by further adding a nucleic acid (preferably e. g., an equimolar mixture of ATP, UTP, GTP and CTP), an antibiotic (preferably sodium penicillin G, streptomycin sulfate or a penicillin-streptomycin solution) and L-glutamine to IMDM can be particularly preferably mentioned.

In the first invention, as particularly preferable mesenchymal cell culturing basic medium, a medium (hereinafter referred to as, "the particularly preferable basic medium in the first invention") prepared by adding 2 mM (final concentration) L-glutamine, a 100 U/mL (final concentration) penicillin-streptomycin solution and ATP, UTP, GTP and CTP (20 μM (final concentration) for each) to IMDM (the composition will be described later); and a medium containing the components of the particularly preferable basic medium in the first invention, in the concentrations which can independently vary within the range of 70% to 130% relative to the concentrations in the basic medium, can be mentioned.

(Composition of IMDM)

0.4 mM glycine, 0.281 mM L-alanine, 0.398 mM L-arginine hydrochloride, 0.167 mM L-asparagine, 0.226 mM L-aspartic acid, 0.381 mM L-cystine dihydrochloride, 0.51 mM L-glutamic acid, 4 mM L-glutamine, 0.2 mM L-histidine hydrochloride monohydrate, 0.802 mM L-isoleucine, 0.802 mM L-leucine, 0.798 mM L-lysine hydrochloride, 0.201 mM L-methionine, 0.4 mM L-phenylalanine, 0.348 mM L-proline, 0.4 mM L-serine, 0.798 mM L-threonine, 0.0784 mM L-tryptophan, 0.462 mM L-tyrosine disodium dihydrate, 0.803 mM L-valine, 0.0000533 mM biotin, 0.0286 mM choline chloride, 0.00839 mM calcium D-pantothate, 0.00907 mM folic acid, 0.0328 mM nicotinic acid amide, 0.0196 mM pyridoxal hydrochloride, 0.00106 mM riboflavin, 0.119 mM thiamine hydrochloride, 0.0000096 mM vitamin B12, 0.04 mM i-inositol, 1.49 mM anhydrous calcium chloride, 0.84 mM anhydrous magnesium sulfate, 4.4 mM potassium chloride, 0.000752 mM potassium nitrate, 36 mM sodium hydrogen carbonate, 77.59 mM sodium chloride, 0.906 mM disodium hydrogen phosphate monohydrate, 0.0000658 mM sodium selenite pentahydrate, 25 mM D-glucose, 25.03 mM HEPES, 0.0399 mM phenol red and 1 mM sodium pyruvate.

As the particularly preferable culture medium to be used in the first invention, a medium prepared by adding an iron ion and an iron transporter to the particularly preferable basic medium in the first invention, can be mentioned. In particular, a medium prepared by adding an iron-bound transferrin as a single active ingredient to the particularly preferable basic medium in the first invention can be more preferably mentioned.

To the culture medium to be used in the first invention, e.g., TPO, BSA, LDL cholesterol, insulin and 2-β-mercaptoethanol can be added. However, if these components are not added, significance of obtaining platelets at lower cost can be more beneficially obtained. To describe it more specifically, conventional MKLI medium long been used in the art contains TPO, BSA, LDL cholesterol, insulin and 2-β-mercaptoethanol (hereinafter these components will be collectively referred to also as a "five components"), which are added to IMDM medium. However, if these five components are not used in the medium to be used in the first invention, megakaryocytes and platelets can be produced at lower cost. The present inventors have experimentally confirmed that none of BSA, LDL cholesterol, insulin and 2-β-mercaptoethanol is required for inducing differentiation of preadipocytes into megakaryocytes and platelets. Note that even if an iron transporter is not present in a medium, if mesenchymal cells can take up an iron ion from the medium into the cells, a "mesenchymal cell culturing basic medium containing an iron ion" can be employed as the culture medium to be used in the first invention in place of the "mesenchymal cell culturing basic medium containing an iron ion and an iron transporter".

The culture conditions in the first invention are not particularly limited as long as platelets can be obtained by culturing mesenchymal cells in the culture medium to be used in the first invention. As the culture temperature, a temperature generally in the range of 12 to 45° C., and preferably 15 to 37° C. can be mentioned. As the culture period, a period generally in the range of 4 to 20 days and preferably 5 to 17 days can be mentioned.

It is preferable that the production method of the first invention further has a step of increasing the number of mesenchymal cells by subjecting the mesenchymal cells to be used in the first invention to maintenance culture before the mesenchymal cells are cultured in the culture medium to be used in the first invention. This is because if the production method has such a maintenance culture step, the number of mesenchymal cells that can be used in the culture medium to be used in the first invention can be increased, as described later, and the yield of platelets relative to the number of mesenchymal cells initially prepared can be remarkably increased. The culture medium to be used in such a maintenance culture is not particularly limited as long as it is a medium in which the mesenchymal cells to be used in the first invention can proliferate. For example, the aforementioned mesenchymal cell culturing basic medium (containing neither iron ion nor iron transporter) can be mentioned. As the maintenance culture, the mesenchymal cell culturing basic medium containing serum and serum components is preferably used. It is preferable that subculture and medium exchange are appropriately performed in the maintenance culture step.

A method for collecting megakaryocytes and platelets from a culture in the first invention is not particularly limited, and a method of separating a culture supernatant containing megakaryocytes and platelets from such a culture can be mentioned. Since the production method of the first invention uses mesenchymal cells (preferably CD31 negative and CD71 positive mesenchymal cells) in place of hematopoietic stem cells, megakaryocytes and platelets can be obtained with high efficiency. In the case of hematopoietic stem cells, even if maintenance culture is carried out before differentiation-inducing culture, the number of cells is scarcely increased; whereas in the case of mesenchymal cells (preferably preadipocytes and subcutaneous adipose tissue-derived mesenchymal stem cells), if the mesenchymal cells are subjected to the maintenance culture step before differentiation induction performed in the culture medium to be used in the first invention, the number of proliferated mesenchymal cells can be 10 to 40 times, preferably 30 to 40 times as large as the number mesenchymal cells initially prepared. If these mesenchymal cells are induced to differentiate, megakaryocytes and platelets can be obtained with high efficiency. Since the differentiation efficiency rates of hematopoietic stem cells and preadipocytes into megakaryocytes and platelets are about 20%, the yield of megakaryocytes and platelets from hematopoietic stem cells is about 20% of the hematopoietic stem cells initially prepared. In contrast, in the mesenchymal cells, a considerably high yield of e.g., about 200 to 800% and preferably about 600 to 800% can be attained. If mesenchymal cells (particularly preadipocytes) are CD31 negative and CD71 positive, since the differentiation efficiency thereof to megakaryocytes and platelets is about 27%, the yield of megakaryocytes and platelets from the mesenchymal cells initially prepared can reach about 270 to 1,080% and preferably about 810 to 1,080%. If the mesenchymal cells (particularly preadipocytes) are CD31 negative, CD71 positive and c-MPL positive, since the differentiation efficiency thereof to megakaryocytes and platelets is about 62%, the yield of megakaryocytes and platelets from the mesenchymal cells initially prepared can reach an extremely high level e.g., 620 to 2,480%, and preferably 1,860 to 2,480%.

The production method of the first invention can further have a step of purifying megakaryocytes and platelets from a culture of the first invention. Such a purification method is not particularly limited; however, e.g., a method of purifying megakaryocytes and platelets by use of an anti-megakaryocyte antibody and an anti-platelet antibody can be mentioned.

The megakaryocytes and platelets of the first invention are not particularly limited as long as they are produced by the production method of the first invention. As the platelets obtained by the production method of the first invention, platelets having a higher thrombus forming ability than those obtained by a conventional production method using hematopoietic stem cells, can be preferably mentioned; and more specifically, platelets containing a number of cells contributing to thrombus formation (measured by thrombus formation analysis) in a ratio of 60 to 85%, and preferably 70 to 85%, can be preferably mentioned. As the megakaryocytes obtained by the production method of the first invention, megakaryocytes, which produce platelets having the aforementioned thrombus forming ability, can be preferably mentioned. Note that the aforementioned ratio of platelets obtained by a conventional production method using hematopoietic stem cells was 52.5±5.3% as described in Example 6 (described later).

(Thrombus Formation Analysis)

As the analysis for thrombus forming ability, the following method can be preferably used. Mesenchymal cells are cultured in the culture medium to be used in the first invention to obtain platelets. A blood sample is prepared by adding platelets ($2 \times 10^4$ cells) obtained in the aforementioned culture to the blood (containing $1 \times 10^5$ of endogenous platelets) taken from an allogeneic vertebrate from which the mesenchymal cells are derived (preferably a spinal animal from which the mesenchymal cells are derived). The blood sample is refluxed to a collagen solid phase chip of a thrombus formation analysis system T-TAS™ (Total Thrombus-formation Analysis System, manufactured by FUJIMORI KOGYO CO. LTD) to form thrombus. Thereafter the percentage (%) of platelets contributing to thrombus formation is obtained.

Megakaryocytes and platelets obtained by the production method of the first invention can be applied to general use as megakaryocytes and platelets. For example, the megakaryocytes alone and the platelets alone or together with pharmaceutically acceptable carrier can be used as blood transfusion preparations such as a platelet preparation, and megakaryocyte-containing preparations. The pharmaceutically acceptable carrier is not particularly limited as long as it does not prevent platelet production from megakaryocytes and thrombus forming ability of platelets. Examples of the carrier include a diluent, an injection agent, a salt, a buffer, a stabilizer, a solubilizer and others known in the art. Of them, a buffer which stabilizes pH of megakaryocyte and platelet preparations in a physiological pH (7.4) range of blood can be preferably mentioned.

As the administration subject for the megakaryocytes and platelets of the first invention and the aforementioned preparation, 1) patients with a bleeding symptom due to e.g., accident and surgery and the accompanying platelet depletion, 2) patients with platelet depletion or a disease accompanying platelet hypofunction and 3) patients with thrombocytopenia as a side effect of medical care such as a chemical treatment or a radiation therapy can be preferably mentioned.

As a method for administering the megakaryocytes and platelets of the first invention and a platelet preparation, a conventional administering method of megakaryocytes, platelets and the aforementioned preparations can be used. Since platelets of the first invention and platelets produced from the megakaryocytes of the first invention have excellent thrombus forming ability, the dose thereof can be reduced from the conventional dose.

As the organism species as an administration subject of the megakaryocytes, platelets of the first invention and the aforementioned preparations, a vertebrate as described above, preferably a mammal, and more preferably a human can be mentioned. The type of vertebrate, from which mesenchymal cells used in producing megakaryocytes are derived, is preferably consistent with the type of vertebrate, to which the megakaryocytes and platelets of the first invention and the aforementioned preparations are to be administered, in order to obtain an excellent thrombus forming effect.

The first invention includes a method for constructing a megakaryocyte and/or platelet bank having the following steps a) to c).

a) providing various types of mesenchymal cells of different HLA types and/or HPA types;

b) selecting predetermined HLA type and/or HPA type of mesenchymal cells among the mesenchymal cells provided in the step a);

c) preparing the predetermined HLA type and/or HPA type of megakaryocytes and/or platelets by the production method of the first invention using mesenchymal cells selected in the step b).

In the patients who have to repeatedly receive platelet transfusion, patients having e.g., bleeding diseases associated with specific genetic abnormalities are included. In the case of these patients, it is not sure whether or not megakaryocytes and platelets are actually produced from patient-derived iPS cells and there is a possibility that platelets alone in which dysfunction remains conserved are produced. In the circumstances, if megakaryocyte and platelet banks, which are based on donation from healthy donors of various HLA types and HPA types and from which megakaryocytes and platelets having different HLA types and HPA types can be prepared, are realized, normal megakaryocytes and platelets having the same HLA type and HPA type as those of the aforementioned patient with gene abnormality can be supplied to the patient. Furthermore, to not only patients with gene abnormality but also patients with bleeding due to, e.g., accidental injury and surgery, megakaryocyte and/or platelet banks in the first invention are advantageous. More specifically, according to the megakaryocyte and/or platelet banks in the first invention, since various types of mesenchymal cells of different HLA types and/or HPA types are previously provided, a step of taking mesenchymal cells from patients themselves is not required and megakaryocytes and platelets can be produced further quickly, with the result that megakaryocytes and platelets having the identical HLA type and/or HPA type to those of the patient can be administered in the stage at which platelet administration is highly required.

The step a) mentioned above is not particularly limited as long as various types of mesenchymal cells of different HLA types and/or HPA types can be provided in the step; however, it is preferable that these different mesenchymal cells prepared are stored in a frozen state in order to immediately use these different mesenchymal cells in culture and store them for a long time. Note that it is preferable that the mesenchymal cells are increased in number by subjecting them to maintenance culture before being frozen and decreased in cell density to some extent, and then, dispensed in e.g., a plurality of frozen vials, and stored. If the cells are stored in this manner, it is possible to avoid the risk: the cells in a specific vial are damaged in a freezing process and fail to engraft after being frozen. In addition, there is an advantage in that when megakaryocytes and platelets are prepared from frozen mesenchymal cells in the step c), the initial rise of proliferation rate is high. This advantage is particularly significantly obtained when the mesenchymal cells, particularly, primary-culture preadipocytes and mesenchymal stem cells known to be divided few times and have a relatively short life, are used.

In order to more efficiently produce megakaryocytes and platelets, mesenchymal cells to be used in a method for constructing a megakaryocyte and/or platelet bank are preferably CD31 negative and CD71 positive mesenchymal cells (preferably preadipocytes) and more preferably CD31 negative, CD71 positive and c-MPL positive mesenchymal cells (preferably preadipocytes).

The mesenchymal cells to be used in a method for constructing a megakaryocyte and/or platelet bank are preferably established mesenchymal cells and more preferably established preadipocytes. This is because if various HLA types and/or HPA types of mesenchymal cells (preferably preadipocytes) are established in advance and a bank of the established mesenchymal cells (preferably preadipocyte strain bank) is prepared, labor, cost and time for taking mesenchymal cells from patients can be saved; in other words, megakaryocytes and platelets having HLA type and/or HPA type, which adapt to those of patients who require administration of megakaryocytes and platelets, can be prepared with less labor and low cost as well as in a short period of time. If a patient has abnormality in gene associated with megakaryocytes and platelets, it is difficult to produce normal megakaryocytes and platelets from patient-derived mesenchymal cells; however, if the aforementioned bank of established mesenchymal cells is used, it is possible to produce megakaryocytes and platelets having the HLA type and/or HPA type adaptable to those of the patient. Note that "established mesenchymal cells" themselves, which are established from mesenchymal cells (preferably established preadipocytes) obtained, are included in the present invention. As a method for establishing such mesenchymal cells, e.g., a known method can be used. As a preferable method for establishing preadipocytes, a method as described in Example 15 can be mentioned, in which preadipocytes are induced to differentiate into mature adipocytes, which are subjected to a ceiling culture method known as a method for establishing mature adipocytes to obtain established preadipocytes.

The step b) is not particularly limited as long as it is a step of selecting predetermined HLA type and/or HPA type of mesenchymal cells among the mesenchymal cells provided in the step a). It is preferable that the HLA type and/or HPA type of mesenchymal cells provided in the step a) are previously identified, because mesenchymal cells having predetermined HLA type and/or HPA type can be quickly selected in the step b). The "predetermined HLA type and/or HPA type" refers to the HLA type and/or HPA type identical, as much as possible, with those of a patient requiring administration of platelets. The case where either one of HLA type or HPA type is identical with that of a patient is included; however, the case where both HLA type and HPA type are identical with those of a patient is particularly preferably included.

The step c) is not particularly limited as long as it is a step of preparing predetermined HLA type and/or HPA type of megakaryocytes and platelets from mesenchymal cells selected in the step b) in accordance with the production method of the first invention. Since the HLA type and HPA type of mesenchymal cells are identical with those types of megakaryocytes and platelets produced from the mesenchymal cells, the step c) is not different from the production method of the first invention except that mesenchymal cells selected in the step b) are used.

[Second Invention]

The method for producing TPO of the second invention (hereinafter referred to simply as "the production method of the second invention") is not particularly limited as long as it is a method including culturing mesenchymal cells or mesenchymal cell-derived megakaryocytes (hereinafter collectively referred to also as "mesenchymal cells and the like") are cultured in the mesenchymal cell culturing basic medium containing an iron ion and an iron transporter and collecting TPO from a culture. The "medium" herein refers to a state of medium obtained by adding water to "medium components" capable of culturing cells. When mesenchymal cells such as preadipocytes are cultured in the mesenchymal cell culturing basic medium containing an iron ion and an iron transporter, the mesenchymal cells are induced to differentiate into megakaryocytes/platelets. During the differentiation process, TPO is conceivably secreted from any one of the mesenchymal cells, megakaryocytes and platelets, two or more selected from these or all three types of cells into the culture medium. The mechanism of secreting TPO from these cells is not yet known; however, it is considered that an iron ion or iron ion and an iron transporter taken in mesenchymal cells and the like promote TPO secretion from the mesenchymal cells and the like in an unknown mechanism.

The mesenchymal cells or mesenchymal cell-derived megakaryocytes to be used in the second invention are not particularly limited as long as they are mesenchymal cells or mesenchymal cell-derived megakaryocytes capable of secreting TPO in the medium by culturing them in the mesenchymal cell culturing basic medium containing an iron ion and an iron transporter. As the mesenchymal cells, e.g., (a) preadipocytes (adipose progenitor cells), (b) mesenchymal stem cells and (c) stromal cells can be mentioned. As the mesenchymal stem cells, subcutaneous adipose tissue-derived mesenchymal stem cells and bone marrow mesenchymal stem cells can be mentioned. As the stromal cells, adipose tissue-derived stromal cells, bone marrow stromal cells, prostate-derived stromal cells and endometrial-derived stromal cells can be mentioned. As the preferable mesenchymal cells, preadipocytes and subcutaneous adipose tissue-derived mesenchymal stem cells can be mentioned. As specific examples of the mesenchymal cells to be used in the second invention, e.g., human primary-culture preadipocytes (HPAd cells), mouse primary-culture progenitor cells (subcutaneous adipose tissue-derived), established mouse stromal cells (OP9 cells), established mouse bone marrow mesenchymal stem cells (HS-22 cells) and established mouse preadipocytes (3T3-L1 cells) can be mentioned. The megakaryocytes are not particularly limited as long as they are mesenchymal cell-derived megakaryocytes. The mesenchymal cells and the like to be used in the second invention can be a cell line or cells taken from a tissue (including primary cultured cell and subcultured cell). Note that if cells and megakaryocytes are those capable of producing TPO in the culture medium by culturing them in the culture medium to be used in the second invention, these cells and megakaryocytes can be applied to the production method of the second invention in place of the mesenchymal cells and the like. For example, if TPO can be produced in the culture medium by culturing megakaryocytes differentiated from stem cells such as iPS cells, in e.g., the culture medium to be used in the second invention (preferably containing TPO), TPO can be produced easily and in a large amount. As a method for obtaining megakaryocytes from iPS cells, for example, the following method can be mentioned. iPS cells are cultured together with auxiliary feeder cells such as OP9 cells to change the shape of the iPS cells to the shape like progenitor hematopoietic stem cells. Thereafter the cells like progenitor hematopoietic stem cells are again cultured together with OP9 cells in culture supplemented with TPO or in MKLI medium containing TPO to obtain megakaryocytes.

As the cell line of mesenchymal cells and the mesenchymal cells taken from a tissue, cells commercially available from companies such as Lonza, PromoCell, CELL APPLICATIONS, and the JCRB cell bank of the National Institute of Biomedical Innovation can be used; however, the mesenchymal cells and the like taken from the tissue of a subject to which TPO obtained by the production method of the second invention is to be administered are preferably used, because if TPO is administered to the subject, a problem of induction of antibodies cross-reacting with endogenous TPO is not produced.

In order to more efficiently produce TPO, the mesenchymal cells and the like to be used in the second invention are preferably CD31 negative and CD71 positive mesenchymal cells and the like (preferably preadipocytes or preadipocyte-derived megakaryocytes) and more preferably CD31 negative, CD71 positive and c-MPL positive mesenchymal cells and the like (preferably preadipocytes or preadipocyte-derived megakaryocytes).

The preadipocytes and subcutaneous adipose tissue-derived mesenchymal stem cells can be taken from a subcutaneous adipose tissue and an adipose tissue such as a visceral tissue; bone marrow mesenchymal stem cells can be taken from a myeloid tissue; and the stromal cells can be taken from an adipose tissue, a myeloid tissue, the prostate and the endometrium. As the aforementioned preadipocytes and subcutaneous adipose tissue-derived mesenchymal stem cells, mesenchymal cells derived from an adipose tissue (preferably subcutaneous adipose tissue) can be preferably mentioned because sampling can be made by less invasive manner and a larger number of mesenchymal cells can be more simply taken. As a method for taking mesenchymal cells from a tissue, an ordinary method can be used. Note that the mesenchymal cell-derived megakaryocytes can be prepared by e.g., culturing mesenchymal cells in the culture medium to be used in the second invention.

The organism species from which the mesenchymal cells and the like are derived, is not particularly limited as long as it is a vertebrate. As the vertebrate, a mammal, a bird, a reptile, an amphibian and fish can be mentioned. Of them, mammals such as a human, a mouse, a rat, a guinea pig, a rabbit, a cat, a dog, a horse, a cow, a monkey, a sheep, a goat and a pig can be preferably mentioned. Of them, a human can be particularly preferably mentioned.

The composition and preferable aspect of the medium to be used in the second invention are the same as in the medium to be used in the first invention.

To the culture medium to be used in the second invention, e.g., TPO, bovine serum albumin (BSA), LDL cholesterol, insulin and 2-β-mercaptoethanol can be added. However, if these components are not added, significance of producing TPO at lower cost can be more beneficially obtained. To describe it more specifically, conventional MKLI medium long been used in the art is prepared by adding TPO, BSA, LDL cholesterol, insulin and 2-β-mercaptoethanol (hereinafter these components will be collectively referred to also as a "five components") to IMDM medium. If these five components are not used in the culture medium to be used in the second invention, TPO can be produced at lower cost. The present inventors have experimentally confirmed that none of BSA, LDL cholesterol, insulin and 2-β-mercaptoethanol is required for inducing differentiation of preadipocytes into megakaryocytes and platelets. (FIG. 5 of the present application). In culturing preadipocytes, if these five components are not used in the culture medium to be used in the second invention, TPO is consistently secreted compared to the case where MKLI medium is used. In addition, TPO can be efficiency produced even if the contents of an iron ion and an iron transporter (preferably iron-bound transferrin) are low. Note that even if an iron transporter is not present in a medium, if mesenchymal cells can take up an iron ion from the medium into the cells, a "mesenchymal cell culturing basic medium containing an iron ion" can be employed as the culture medium to be used in the second invention in place of the "mesenchymal cell culturing basic medium containing an iron ion and an iron transporter".

The culture conditions in the second invention are not particularly limited as long as TPO can be produced by culturing mesenchymal cells and the like in the culture medium to be used in the second invention. As the culture temperature, a temperature generally in the range of 12 to 45° C., and preferably 15 to 37° C. can be mentioned. As the culture period, a period generally in the range of 3 to 8 days, and preferably 4 to 7 days can be mentioned. If the culture period is extremely long, since TPO is again e.g., taken in cells, TPO concentration of the culture medium tends to be low.

It is preferable that the production method of the second invention further has a step of increasing the number of mesenchymal cells by subjecting the mesenchymal cells or the mesenchymal cells before being induced into the megakaryocytes, to maintenance culture before the mesenchymal cells and mesenchymal cell-derived megakaryocytes are cultured in the culture medium to be used in the second invention. This is because if the production method has such a maintenance culture step, the number of proliferated mesenchymal cells can be 10 to 40 times, preferably 30 to 40 times as large as the number of mesenchymal cells (preferably preadipocytes and subcutaneous adipose tissue-derived mesenchymal stem cells) initially prepared; and if these mesenchymal cells and the mesenchymal cell-derived megakaryocytes are subjected to the production method of the second invention, the yield of TPO per 1 mL of medium (culture supernatant) after culture can be remarkably increased. The culture medium to be used in maintenance culture is not particularly limited as long as it is a medium in which the mesenchymal cells to be used in the present invention can proliferate. For example, the aforementioned mesenchymal cell culturing basic medium (containing neither an iron ion nor an iron transporter) can be mentioned. When maintenance culture is carried out, it is preferable to use a mesenchymal cell culturing basic medium containing serum and serum components. It is preferable that subculture and medium exchange are appropriately performed in the maintenance culture step.

The method for taking TPO from a culture in the second invention is not particularly limited. A method of separating a culture supernatant containing TPO from a culture can be mentioned. In the production method of the second invention, TPO can be obtained with high efficiency. For example, the yield of TPO (dry weight) per 1 mL of medium (culture supernatant) after culture can reach 30 pg to 100 pg.

The production method of the second invention can further have a step of purifying TPO from a culture of the second invention. Such a purification method is not particularly limited and, for example, a method of purifying TPO using a TPO receptor, namely a c-MPL receptor, (Japanese Unexamined Patent Application Publication (see, Translation of PCT Application) No. H10-511681) and a method of purifying TPO using a specific antibody against TPO can be preferably mentioned.

TPO obtained by the production method of the second invention can be used as a platelet production inducer, a platelet production promoter and a prophylactic or therapeutic agent (hereinafter these three agents will be collectively referred to as "agent of the second invention") for diseases with platelet depletion or platelet hypofunction (hereinafter referred to as, "thrombocytopenia and the like"), which have been established uses of TPO. More specifically, if TPO is allowed to act on e.g., hematopoietic stem cells in vitro, in vitro platelet production is induced or promoted to obtain platelets with high efficiency. If TPO is allowed to act on e.g., hematopoietic stem cells in vivo, in-vivo platelet production is induced or promoted, with the result that thrombocytopenia and the like can be prevented and treated.

TPO obtained by the production method of the second invention can be directly used as a platelet production inducer, a platelet production promoter and a prophylactic or therapeutic agent for thrombocytopenia and the like; however, TPO can be formed into an appropriate preparation by an ordinary method. The dosage form of the preparation can be a solid such as a powder and a granule; however, in order to obtain more excellent platelet production-inducing effect, platelet production promoting effect, a prophylactic or therapeutic effect of thrombocytopenia and the like, the dosage form is preferably a liquid such as a solution, an emulsion and a suspension. As a method for producing the liquid, for example, a method of mixing TPO with a solvent and a method of mixing with a suspending agent and an emulsifier can be preferably mentioned. When TPO of the second invention is formed into a preparation as mentioned above, if necessary in forming a preparation, an appropriate pharmaceutically acceptable carrier such as an excipient, a binder, a solvent, a solubilizing agent, a suspending agent, an emulsifying agent, an isotonic agent, a buffering agent, a stabilizing agent, a soothing agent, a preservative, an antioxidant, a coloring agent, a lubricant, a disintegrant, a wetting agent, an adsorbent, a sweetening agent and a diluent can be blended as an optional component. Note that when the platelet production inducer and a platelet production promoter are used in vitro, a culture supernatant containing TPO can be directly used as a platelet production inducer and a platelet production promoter.

When the platelet production inducer and platelet production promoter are used in vitro, each agent can be used by adding it to the basic medium for culturing e.g., hematopoietic stem cells. As the concentration of each agent to be added to the basic medium, the range from 1 ng/mL to 2.5 µg/mL, preferably the range from 5 ng/mL to 500 ng/mL in terms of the dry-state TPO equivalent concentration can be mentioned.

When the agent of the second invention and a prophylactic or therapeutic agent of the second invention are used in vivo, they can be used by administering it to a vertebrate, preferably a mammal and more preferably a human. Such an administration method is not particularly limited and e.g., intravascular administration (preferably intravenous administration), intraperitoneal administration, intestinal administration and subcutaneous administration can be preferably mentioned. Of them, intravascular administration can be preferably mentioned and particularly intravenous administration can be further preferably mentioned.

The dose of the agent of the second invention can vary depending upon e.g., the type of thrombocytopenia and the like, the degree of symptom thereof, the dosage form and the weight of the subject to be administered; however, for example, the range from 0.2 µg/kg to 20 mg/kg per day in terms of the dry-state TPO equivalent, and particularly the range from 0.4 µg/kg to 10 mg/kg can be more preferably mentioned. Note that the dosage of the agent of the second invention per day can be administered once or in a plurality of doses. It is preferable that the agent of the second invention is continuously administered, for example, administration is continuously made twice or more at a frequency of at least once every three days, more preferably three times or more at a frequency of at least once every two days, and further preferably four times or more at a frequency of at least once every day.

As the subject to which the agent of the second invention is to be administered, a vertebrate as mentioned above, preferably a mammal, and more preferably a human can be mentioned. The type of vertebrate, from which mesenchymal cells and the like to be used in producing TPO contained in the agent of the second invention are derived, is preferably consistent with the type of vertebrate, which is a subject to which the agent of the second invention is to be administered, in order to obtain more excellent platelet production inducing effect, platelet production promoting effect and prophylactic or therapeutic effect on thrombocytopenia and the like.

Note that, as other aspects of the second invention, use of "TPO obtained by the production method of the second invention" for preparing the agent of the second invention, use of "TPO obtained by the production method of the second invention" for prophylaxis or therapy of thrombocytopenia and the like, and a method for preventing and treating thrombocytopenia and the like by administrating "TPO obtained by the production method of the second invention" to a target vertebrate can be mentioned.

[Third Invention]

The method for producing TPO of the third invention (hereinafter referred to simply as "the production method of the third invention") is not particularly limited as long as it is a method including culturing preadipocytes in the preadipocyte culturing basic medium containing a differentiation-inducing agent (hereinafter referred to simply as a "differentiation-inducing agent") into mature adipocytes and collecting thrombopoietin from a culture. The "medium" used herein refers to a state of medium obtained by adding water to "medium components" capable of culturing cells. When preadipocytes are cultured in the preadipocyte culturing basic medium containing the aforementioned three components, the preadipocytes are induced to differentiate into adipose cells (mature adipocyte) and TPO is secreted during the differentiation based on unknown mechanism.

The preadipocytes used in the third invention are the same as in the second invention. In order to more efficiently produce TPO, the preadipocytes used in the third invention are preferably CD31 negative and CD71 positive preadipocytes, and more preferably CD31 negative, CD71 positive and c-MPL positive preadipocytes.

The medium (hereinafter referred to as, "the culture medium to be used in the third invention") to be used in the culture according to the third invention is a medium prepared by adding a differentiation-inducing agent to the preadipocyte culturing basic medium. The "differentiation-inducing agent into mature adipocytes" in the third invention refers to a substance or composition inducing differentiation of preadipocytes into mature adipocytes. As such a differentiation-inducing agent, known agents can be used. For example, one or more (preferably 3 or more, more preferably 4 or more) selected from the group consisting of 3-isobutyl-1-methylxanthine (simply referred to as "isobutylmethylxanthine"); insulin; dexamethasone; an indole derivative such as indomethacin; and a thiazole derivative such as rosiglitazone and pioglitazone (see, Japanese Unexamined Patent Application Publication No. 2010-193721) can be mentioned. Of them, one or more (preferably 3 or more) selected from the group consisting of isobutylmethylxanthine, insulin, dexamethasone and indomethacin can be preferably mentioned. Of them, a combination of four types: isobutylmethylxanthine, insulin, dexamethasone and indomethacin can be particularly preferably mentioned. As these differentiation-inducing agents, commercially available ones can be used.

The concentration of the differentiation-inducing agent in the culture medium to be used in the third invention is appropriately controlled in accordance with the differentiation-inducing agent to be used. The concentration of isobutylmethylxanthine is usually about 10 to 1000 µM and preferably about 250 to 750 µM. The concentration of insulin is about 0.1 to 10 µM and preferably about 0.5 to 2.5 µM. The concentration of dexamethasone is about 0.1 to 10 µM and preferably about 0.5 to 2.5 µM. The concentration of an indole derivative such as indomethacin is about 10 to 500 µM and preferably about 50 to 300 µM. The concentration of a thiazole derivative is about 0.1 to 10 µM and preferably about 0.5 to 5 µM.

The preadipocyte culturing basic medium in the third invention is not particularly limited as long as it is a medium capable of producing TPO by culturing preadipocytes in the medium supplemented with the differentiation-inducing agent into mature adipocytes; however, the basic medium is preferably a chemical synthesized medium since it is easily prepared and variation from lot to lot can be prevented. The basic medium preferably contains one or more types of sugars, one or more types of inorganic salts, one or more types of amino acids and one or more types of vitamins and one or more types of other components. The composition and preferable aspect of the preadipocyte culturing basic medium are the same as those in the first and second inventions. However, in the third invention, it is preferable to add serum and serum components to the preadipocyte culturing basic medium not only for maintenance culture of preadipocytes but also for differentiation induction of preadipocytes into mature adipocytes. As such serum and serum components, fetal bovine serum can be preferably contained in a final concentration within the range of 5 to 25% in the medium.

The culture conditions in the third invention are not particularly limited as long as TPO is produced by culturing preadipocytes in the culture medium to be used in the third invention. As the culture temperature, a temperature generally in the range of 12 to 45° C., preferably 15 to 37° C. can be mentioned. As the culture period, a period generally in the range of 4 to 20 days and preferably 5 to 17 days can be mentioned. As the $CO_2$ concentration, a $CO_2$ concentration within the range of 3 to 8% and preferably a $CO_2$ concentration of 5% can be mentioned.

It is preferable that the production method of the third invention further has a step of increasing the number of preadipocytes to be used in the third invention by subjecting them to maintenance culture before culturing the preadipocytes in the culture medium to be used in the third invention. This is because if the method has such a maintenance culture step, the number of proliferated preadipocytes can be 10 to 40 times, preferably 30 to 40 times as large as the number preadipocytes initially prepared, and because if these preadipocytes are subjected to the production method of the third invention, the yield of TPO per 1 mL of medium (culture supernatant) after culture can be remarkably increased. The culture medium to be used in maintenance culture is not particularly limited as long as it is a medium in which the preadipocytes to be used in the present invention can proliferate. For example, the aforementioned preadipocyte culturing basic medium (containing none of the above differentiation-inducing agents) can be mentioned. In the maintenance culture step, it is preferable that subculture and medium exchange are appropriately carried out.

The method for taking TPO from a culture in the third invention is the same as in the method for taking TPO from a culture in the second invention. The production method of the third invention can further have a step of purifying TPO from a culture of the third invention. The purification method is the same as described in the second invention.

TPO obtained by the production method of the third invention is not particularly different from TPO obtained by the production method of the second invention and can be used in the same use of TPO as mentioned in the second invention. Note that as other aspects of the third invention, use of "TPO obtained by the production method of the third invention" for preparing the agent of the third invention, use of "TPO obtained by the production method of the third invention" for prophylaxis or therapy of thrombocytopenia and the like, and a method for preventing and treating thrombocytopenia and the like by administrating "TPO obtained by the production method of the third invention" to a target vertebrate can be mentioned.

The present invention will be more specifically described by way of Examples below; however, the present invention is not limited to these Examples. Note that Examples 1 to 8 and 15 are related to the first invention, Examples 9 to 15 to the second invention, and Example 16 to the third invention.

Example 1

[Production of Megakaryocytes/Platelets from Mesenchymal Cells]

Human primary-culture preadipocytes (HPAd) were purchased from CELL APPLICATIONS (San Diego, Calif.). Maintenance culture was carried out in a medium prepared by adding a 10% fetal bovine serum (manufactured by Sigma), a non-essential amino acid(s) (manufactured by Life Technology) and a 100 U/mL penicillin-streptomycin solution (manufactured by Life Technology) to DMEM medium (Dulbecco's Modified Eagle's Medium, manufactured by Life Technology). Subculture was carried out every three days and diluted double. Cells were removed using a 0.05% trypsin solution (manufactured by Life Technology). The medium was exchanged every two days.

Mouse stromal cells (OP9 cells) were provided by Graduate Schools of Osaka University. Maintenance culture was carried out in a medium prepared by adding 20% fetal bovine serum (NICHIREI CORPORATION) to α MEM (Minimum Essential Media, manufactured by Life Technology).

A medium (MKLI medium) for inducing human preadipocytes and mouse stromal cells to differentiate into megakaryocytes/platelets was prepared. MKLI medium was prepared by adding 2 mM L-glutamine (manufactured by Life Technology), a 100 U/mL penicillin-streptomycin solution (manufactured by Life Technology), 0.5% BSA (manufactured by Sigma), 4 µg/mL LDL cholesterol (manufactured by Sigma), 200 μg/mL iron-saturated transferrin (manufactured by Sigma), 10 μg/mL insulin (manufactured by Sigma), 50 μM 2-β-mercaptoethanol (manufactured by Life Technology), nucleotides (ATP, UTP, GTP, and CTP, 20 μM for each) (manufactured by Life Technology) and 50 ng/mL human thrombopoietin (TPO, manufactured by Stem Cell Technologies) to IMDM medium (Iscove's Modified Dulbecco's Medium, manufactured by Life Technology).

The mouse stromal cells (OP9 cells) and human preadipocytes (HPAd cells) were each seeded at a ratio of 5,000 cells/cm$^2$ on MKLI medium and cultured to differentiate the cells. Immediately after initiation of differentiation culture of individual types of cells, on Day 7 and Day 10 after initiation of the culture were analyzed for shape by an optical microscope. The results are shown in FIG. 1. In both cases of the mouse stromal cells and human preadipocytes, large cells, i.e., megakaryocyte-like cells were observed on Day 7 and Day 10 (shown in white boxes).

Human preadipocytes on Day 8 after differentiation culture were stained with a dye for staining cellular nucleus, i.e., PI (Propidium iodide, manufactured by Sigma) and measured by use of flow cytometry. The results are shown in FIG. 2 (left). In the human preadipocytes on Day 8 after differentiation culture, it was demonstrated that multinuclearity, which is a characteristic feature of megakaryocytes, took place.

Human preadipocytes on Day 10 after differentiation culture were directly labeled with PE (R-phycoerythrin)-labeled anti-CD41 antibody (manufactured by BD Sciences) and FITC-labeled anti-CD42b antibody (manufactured by BD Sciences) and measured by flow cytometry. The results are shown in FIG. 2 (right). Both CD41 (platelet glycoprotein IIb) and CD42b (platelet glycoprotein Ibα) are specific markers for megakaryocytes and platelets. On Day 10 after differentiation culture, cells of the human preadipocytes expressing both CD41 and CD42b are observed.

Example 2

[Function of Megakaryocytes/Platelets Produced from Preadipocytes]

To check whether megakaryocytes/platelets produced from preadipocytes each have a function, platelet producibility and thrombus forming ability were analyzed in blood flow. FIG. 3 is a schematic illustration how to analyze the thrombus forming ability. First, a mouse subcutaneous adipose tissue was isolated. To the tissue, collagenase was added. The mixture was incubated at 37° C. for one hour, centrifuged to obtain a cell layer as a lower layer. Thereafter, as described in Example 1, these cells were subjected to subculture carried out in maintenance medium three times. Megakaryocytes differentiated by the same method were labeled with a fluorescent dye, CFSE (5-(and 6)-carboxyfluorescein diacetate succinimidyl ester, manufactured by DOJINDO LABORATORIES). The mouse was irradiated with radiation (2 grays) to obtain a thrombocytopenia mouse, to which 5×10$^6$ megakaryocytes labeled with CFSE were transfused. Then, blood was taken from the mouse, stained with a PE-labeled anti-CD41 antibody and analyzed by flow cytometry. As a result, the presence of CFSE and CD41 double positive cells was confirmed. In this manner, the platelet release ability of CFSE-labeled megakaryocytes in the body of the mouse was confirmed. Subsequently, a whole-blood sample containing platelets was taken and thrombus forming ability in blood flow was analyzed by a thrombus formation analysis system T-TAS™ (Total Thrombus-formation Analysis System, manufactured by FUJIMORI KOGYO Co., Ltd.).

FIG. 4 (upper stages) shows the results of blood samples obtained from the thrombocytopenia mouse, to which the megakaryocytes labeled with CFSE were transfused, and analyzed by T-TAS. It was successfully confirmed that thrombus was formed on chips (FIG. 4, upper stage, left). It was found that platelets attached with a fluorescence label were incorporated in thrombus (FIG. 4 upper stage, right). In contrast, when collagen solid-phase chips for measurement (FIG. 4, lower-stage, left), and blood samples of a thrombocytopenia mouse to which megakaryocytes were not transfused (FIG. 4, lower-stage, right) were analyzed for thrombus forming ability, it was confirmed that thrombus was not formed.

From the foregoing, it has been demonstrated that the megakaryocytes and platelets differentiated from preadipocytes by the production method of the present invention have a physiological function; in other words, the megakaryocytes have platelet producibility, and the platelets and platelets produced from the megakaryocytes have a thrombus forming ability.

Example 3

[Identification of Megakaryocytes/Platelet Production Inducing Substance]

In order to identify an important factor(s) for inducing production of megakaryocytes/platelets from preadipocytes, mediums were prepared by separately adding individual reagents contained in a differentiation-inducing medium (MKLI medium) for megakaryocytes/platelets, to a basic medium (IMDM medium containing 2 mM L-glutamine, a 100 U/mL penicillin-streptomycin solution, and nucleotides (ATP, UTP, GTP, and CTP, 20 μM for each)). More specifically, five types of mediums were prepared by adding 0.5% bovine serum albumin, 10 μg/mL insulin, 4 μg/mL LDL cholesterol, 200 μg/mL iron-saturated transferrin (iron-bound transferrin) and 50 μM 2-β-mercaptoethanol, respectively, to the basic mediums (FIG. 5). Mouse preadipocytes maintenance-cultured in accordance with the method of Example 1 were cultured in the above five types of mediums and in the basic medium, i.e., in total 6 types of medium (FIG. 5) for 7 days.

The mouse preadipocytes on Day 7 after culture in each of the mediums were directly labeled with a FITC-labeled anti-CD41 antibody and analyzed by flow cytometry. As a result, in a medium prepared by adding BSA, LDL cholesterol, insulin or 2-β-mercaptoethanol to the basic medium, cells expressing CD41, i.e., a specific marker of megakaryocytes/platelet, were not observed; whereas cells expressing CD41, a specific marker of megakaryocytes/platelet, were observed only in the medium prepared by adding iron-bound transferrin to the basic medium, demonstrating that megakaryocytes/platelets are produced (FIG. 5).

In consideration of the results, whether a transferrin receptor CD71 knock-down preadipocytes have differentiation potency to megakaryocytes and platelets or not was checked. To human preadipocytes, a gene of siRNA of CD71 (siRNA-CD71) (the sequence of a sense strand is represented by SEQ. ID No. 1, whereas the sequence of the antisense strand is represented by SEQ. ID No. 2) or a scrambled oligo (negative control) (the sequence of a sense strand is represented by SEQ. ID No. 3, whereas the sequence of the antisense strand is represented by SEQ. ID No. 4) was introduced. Forty eight hours later, the human preadipocytes were cultured in a medium prepared by adding transferrin alone to the basic medium, for four days.

Human preadipocytes on Day 4 after culture were directly labeled with a FITC-labeled anti-CD41 antibody and analyzed by flow cytometry. As a result, production of megakaryocytes and platelets was not observed in CD71 knockdown human preadipocytes (Table 1). From this, it has been clearly demonstrated that a pathway via a transferrin receptor is required for inducing megakaryocytes/platelets from preadipocytes.

TABLE 1

|  | Day 0 (48 hours after siRNA introduction) | | Day 4 | |
| --- | --- | --- | --- | --- |
|  | CD71 % | CD41 % | CD71 % | CD41 % |
| siRNA-CD71 | 5.7 ± 0.2 | 0.1> | 7.5 ± 0.7 | 0.1> |
| Negative control | 14.6 ± 0.2 | 0.3 ± 0.1 | 13.8 ± 0.9 | 9.5 ± 1.3 |

Example 4

[Investigation on Concentration of Iron-Bound Transferrin]

Human preadipocytes maintenance-cultured in accordance with the method of Example 1 were prepared and cultured in mediums prepared by adding iron-bound transferrin samples different in concentration to the basic medium described in Example 3. The ratio (%) of CD41 (specific marker of megakaryocytes and platelets)-positive cells in the cells on Day 4 after initiation of the culture was determined. The results are shown in Table 2.

TABLE 2

| | Iron-bound transferrin (μg/mL) | | | | | |
| --- | --- | --- | --- | --- | --- | --- |
|  | 0 | 25 | 50 | 100 | 200 | 400 |
| CD41 (%) | 0.1> | 15.5 ± 9.2 | 18 ± 9.9 | 17.5 ± 9.2 | 19 ± 8.5 | 11 ± 7.1 |

From the results, it has been demonstrated that even if the concentration of iron-bound transferrin is lower than that (200 μg/mL), in conventional MKLI medium, more specifically even if an iron-bound transferrin concentration is less than 25 to 200 μg/mL (preferably less than 50 to 200 μg/mL), megakaryocytes and platelets are produced in the same level as that produced at the iron-bound transferrin concentration of 200 μg/mL.

Example 5

[Effect of Iron Chelator and Apo-Transferrin Added to Culture Medium]

To investigate effect of an iron ion on induction of preadipocytes into megakaryocytes/platelets, analysis using the preadipocytes was made. Specifically, a medium (basic medium+iron-bound transferrin+Desferal (deferoxamine mesylate)) was prepared by adding an iron chelator, Desferal (deferoxamine mesylate, manufactured by Novartis Pharma K. K.) to a basic medium containing 200 μg/mL iron-bound transferrin, or a medium (basic medium+apo-transferrin) was prepared by adding a non-iron-bound transferrin, apo-transferrin (manufactured by Athens Research and Technology) to a basic medium alone. Cells were cultured in these mediums and the ratio (%) of CD41 (specific marker of megakaryocytes and platelets)—positive cells in the cells on Day 4 after the culture was determined. The results of Desferal (deferoxamine mesylate) addition are shown in Table 3; whereas the results of apo-transferrin addition are shown in Table 4.

TABLE 3

| | Desferal (mg/mL) | | | | | |
| --- | --- | --- | --- | --- | --- | --- |
| | 0 | 0.005 | 0.05 | 0.5 | 5 | 50 |
| CD41 (%) | 52 ± 9.9 | 36 ± 11.3 | 35.5 ± 10.6 | 14 ± 5.7 | 10.5 ± 6.4 | 5 ± 2.8 |

TABLE 4

| | Apo-transferrin (μg/mL) | |
| --- | --- | --- |
| | 200 | 400 |
| CD41 (%) | 16.5 ± 4.95 | 14.5 ± 3.54 |

As is apparent from the results of Table 3 and Table 4, the ratio of CD41 (specific marker of megakaryocytes and platelets)-positive cells decreases depending upon the addition amounts of the iron chelator and apo-transferrin. From the above, it was demonstrated that an iron ion and an iron transporter are very important to produce megakaryocytes and platelets from mesenchymal cells such as preadipocytes, and in particular, at least an iron ion is essential.

Example 6

[Comparison of Thrombus Forming Ability Between Preadipocyte-Derived Platelets and Hematopoietic Stem Cell-Derived Platelets]

To compare thrombus forming ability of preadipocyte-derived platelets and that of hematopoietic stem cell-derived platelets, the following experiment was carried out.

Hematopoietic stem cells derived from a tissue of a C57BL/6 lineage mouse were cultured in TPO (50 ng/mL)-containing MKLI medium (note that TPO used herein was purchased from Stem Cell Technologies) to induce differentiation of them into platelets and platelets were obtained. To the blood (containing $1 \times 10^5$ of endogenous platelets)

taken from the mouse, the platelets ($2 \times 10^4$ cells) prepared by the differentiation induction as mentioned above were added to prepare a blood sample. Another blood sample was prepared in the same manner as above except that preadipocytes derived from a tissue of the same C57BL/6 lineage mouse was used in place of the hematopoietic stem cells, and TPO-free MKLI medium was used in place of TPO-containing MKLI medium. Both blood samples were separately refluxed to a collagen solid phase chip of a thrombus formation analysis system T-TAS™ (Total Thrombus-formation Analysis System, manufactured by FUJIMORI KOGYO Co., Ltd.) to form thrombus and then the percentage (%) of platelets contributing to thrombus formation was obtained. As a result, in the sample of hematopoietic stem cell-derived platelet, the ratio was 52.5±5.3%; whereas in the sample of preadipocyte-derived platelets, the ratio was 77.8±5.1%, demonstrating that the ratio of platelets contributing to thrombus formation is significantly (P=0.0257) higher in the preadipocyte-derived platelets. From this, it has been strongly suggested that the platelet transfusion effect obtained by the hematopoietic stem cell-derived platelets can be obtained by a lower number of preadipocyte-derive platelets.

Example 7

[Effect of c-MPL Inhibition Antibody on Production of Megakaryocytes and Platelets from Preadipocytes]

To investigate the function of thrombopoietin (TPO) and a thrombopoietin receptor (c-MPL) in production of megakaryocytes/platelets from preadipocytes, the following experiment was carried out.

A thrombopoietin receptor, i.e., c-MPL, is activated when thrombopoietin is bound thereto and then a signaling pathway in which c-MPL is involved is activated. As a monoclonal antibody inhibiting the function of human c-MPL, AMM2 antibody (manufactured by Immuno-Biological Laboratories (IBL)) was prepared. In addition, human preadipocytes maintenance-cultured in accordance with the method of Example 1 were prepared.

In a medium prepared by adding 200 µg/mL iron-bound transferrin and 5 µg/mL or 10 µg/mL AMM2 antibody to the basic medium described in Example 3, the aforementioned human preadipocytes were cultured for 4 days. In addition, the human progenitor cells were cultured in the same manner as above except that AMM2 antibody was not added. The cells of these 3 types of cultures were directly labeled with FITC-labeled anti-CD41 antibody and the number of CD41-positive cells was determined by flow cytometry. The results are shown in FIG. 6.

As is apparent from FIG. 6, as the concentration of the AMM2 antibody in the medium increased, the number of the CD41 (specific marker of megakaryocytes/platelets)-positive cells decreased. From this, it has been clearly demonstrated that a pathway via a thrombopoietin receptor is required to induce megakaryocytes and platelets from preadipocytes.

Example 8

[Identification of Cell Surface Antigen of Cells Efficiently Differentiated into Platelets]

To identify a surface antigen(s) of preadipocytes efficiently differentiated into platelets, the following experiment was carried out.

A subcutaneous adipose tissue was isolated from a mouse. To this, collagenase was added. The mixture was incubated at 37° C. for one hour and centrifuged to obtain a cell layer as a lower layer. Thereafter, these cells were labeled with a fluorescence-labeled anti-CD45 antibody (manufactured by BD Bioscience), a fluorescence-labeled anti-Ter119 antibody (manufactured by BD Bioscience) and 7AAD (manufactured by BD Bioscience), and fluorescence was measured by flow cytometry. The results are shown in FIG. 7, upper right panel. Of the cells shown in FIG. 7, upper right panel, cells of CD45 negative, Ter119 negative and 7-AAD negative (cells under the line at the center of the upper right panel of FIG. 7) were separately taken. CD45 is known as a marker of hematopoietic cells (leucocytes, lymphocytes, eosinophils, monocytes, basophils, and neutrophils) excluding erythrocytes and platelets. Ter119 is known as a marker of mature erythrocytes and erythroid progenitor cells. 7-AAD (7-amino-actinomycin D) is known as a marker of dead cells.

Subsequently, CD45 negative, Ter119 negative and 7-AAD negative cells separately taken were labeled with a fluorescence-labeled anti-CD31 antibody (manufactured by BD Bioscience) and fluorescent was measured by flow cytometry. The results are shown in FIG. 7, lower left panel. Of the cells shown in the lower left panel of FIG. 7, CD31 negative cells (cells under the line of the center of the lower left panel of FIG. 7) were separately taken. CD31 is known as a marker of vascular endothelial cells.

Subsequently, the cells (CD45 negative, Ter119 negative, 7-AAD negative and CD31 negative) previously separately taken were labeled with a fluorescence-labeled anti-c-MPL antibody (manufactured by BD Bioscience) and a fluorescence-labeled anti-CD71 antibody (manufactured by BD Bioscience), and fluorescence was measured by flow cytometry. The results are shown in FIG. 7 (lower right panel) and FIG. 8 (left panel). Of the cells shown in the left panel of FIG. 8, cells in lower left (c-MPL negative and CD71 negative), lower right (c-MPL negative and CD71 positive) and upper right (c-MPL positive and CD71 positive) portions were separately taken.

The cells shown in individual portions of the left panel of FIG. 8 were separately cultured in a medium prepared by adding 200 µg/mL iron-bound transferrin to the basic medium described in Example 3. The ratio (%) of CD41 (specific marker of megakaryocytes/platelets)-positive cells in the cells on Day 5 after initiation of culture was determined. The results are shown in FIG. 8, right (upper right panel, right center panel, lower right panel). The lower right panel of FIG. 8 shows the detection result of CD41 positive cells and its ratio (10.8%) when cells (CD45 negative, Ter119 negative, CD31 negative, c-MPL negative and CD71 negative cells) (more specifically, CD31 negative, c-MPL negative and CD71 negative preadipocytes) shown in the lower left portion of the left panel of FIG. 8 were cultured. The right center panel of FIG. 8 shows the detection result of CD41 positive cells and its ratio (26.9%) when cells (CD45 negative, Ter119 negative, CD31 negative, c-MPL negative and CD71 positive cells) (more specifically, CD31 negative, c-MPL negative and CD71 positive preadipocytes) shown in the lower right portion of the left panel of FIG. 8 were cultured. The upper right panel of FIG. 8 shows the detection result of CD41 positive cells and its ratio (62.3%) when cells (CD45 negative, Ter119 negative, CD31 negative, c-MPL positive and CD71 positive cell) (more specifically, CD31 negative, c-MPL positive and CD71 positive preadipocytes) shown in the upper right portion of the left panel of FIG. 8 were cultured. As described above, CD31 negative, c-MPL negative and CD71 positive preadipocytes and CD31 negative, c-MPL positive and CD71 positive preadipocytes had a significantly high (2.5 times or more) induction efficiency to megakaryocytes/platelets, compared to CD31 negative, c-MPL negative and CD71 negative preadipocytes. Of them, CD31 negative, c-MPL positive and CD71 positive preadipocytes had a significantly high induction efficiency to megakaryocytes/platelets, which was about 5.8 times as high as CD31 negative, c-MPL negative and CD71 negative preadipocytes.

Based on the experiment of Example 8, it has been demonstrated that CD31 negative, c-MPL negative and CD71 positive preadipocytes and CD31 negative, c-MPL positive and CD71 positive preadipocytes are efficiently differentiated into megakaryocytes/platelets, and that CD31 negative, c-MPL positive and CD71 positive preadipocytes are particularly efficiency differentiated into megakaryocytes/platelets.

Example 9

[TPO Production Associated with Differentiation Induction of Preadipocytes into Megakaryocytes/Platelets]

First, a differentiation-inducing medium ("MKLI medium-TPO") into megakaryocytes/platelets was prepared. The composition of the differentiation-inducing medium is equivalent to the composition prepared by removing TPO alone from MKLI medium (see, for example, non-patent document 9, page 251, 2.2) and is more specifically as follows.

A medium prepared by adding 2 mM L-glutamine (manufactured by Life Technology), a 100 U/mL penicillin-streptomycin solution (manufactured by Life Technology), 0.5% bovine serum albumin (manufactured by Sigma), 4 µg/mL LDL cholesterol (manufactured by Sigma), 200 µg/mL iron saturated transferrin (iron-bound transferrin) (manufactured by Sigma), 10 µg/mL Insulin (manufactured by Sigma), 50 µM 2-β-mercaptoethanol (manufactured by Life Technology) and nucleotides (ATP, UTP, GTP, and CTP, 20 µM for each) (manufactured by Life Technology), to IMDM medium (Iscove's Modified Dulbecco's Medium, manufactured by Life Technology).

Mouse primary-culture preadipocytes were isolated from a mouse subcutaneous adipose tissue. To the preadipocytes, collagenase was added and the resultant preadipocytes were incubated at 37° C. for one hour, centrifuged to obtain a cell layer as an underlayer. Human primary-culture preadipocytes (Human Preadipocytes: HPAd) were purchased from CELL APPLICATIONS (San Diego, Calif.). The maintenance culture of both preadipocytes were carried out in a medium prepared by adding 10% fetal bovine serum (manufactured by Sigma), a non-essential amino acid(s) (manufactured by Life Technology) and a 100 U/mL penicillin-streptomycin solution (manufactured by Life Technology) to DMEM medium (Dulbecco's Modified Eagle's Medium, manufactured by Life Technology). A subculture was carried out every three days and diluted double. Cells were removed by using a 0.05% trypsin solution (manufactured by Life Technology). The medium was exchanged every two days.

The mouse and human preadipocytes ($10^6$ cells) obtained were cultured in 2 mL of "MKLI medium-TPO" for 12 days. The TPO concentration in each of the culture supernatants was measured immediately after initiation of culture of the preadipocytes, and Day 7 and Day 12 after initiation of culture of the preadipocytes, by ELISA quantitation using the TPO Quantikine ELISA kit (manufactured by R&D Systems). The results of the case using the mouse preadipocytes are shown in Table 5. From the results, it has been clearly demonstrated that TPO secretion is stimulated by differentiation induction of preadipocytes into megakaryocytes/platelets.

TABLE 5

| After differentiation induction | Day 0 | Day 7 | Day 12 |
|---|---|---|---|
| TPO in culture supernatant (pg/mL) | Below detection limit | 170.1 ± 8.1 | 8 ± 2 |

Example 10

[Platelets Production Activity of TPO Produced]

Activity of TPO secreted during the process of producing megakaryocytes/platelets from preadipocytes was investigated based on the presence or absence of differentiation-inducing property of mouse hematopoietic stem cells into megakaryocytes/platelets when TPO was used. Whether platelets are produced or not was checked based on the shape analyzed by an optical microscope and flow-cytometric expression analysis of platelet specific marker CD41. These results are shown in FIG. 9.

The upper-stage panels of FIG. 9 show the results of hematopoietic stem cells cultured in the culture supernatant (TPO concentration: 43.1±4.9 pg/mL) obtained from culture of preadipocytes in "MKLI medium-TPO". Platelets were produced on either one of Day 2 and Day 8 after initiation of culture of the hematopoietic stem cells. The ratio of CD41 positive cells on Day 8 increased up to 15.2% from the ratio (1.26%) thereof in hematopoietic stem cells before culture.

The middle-stage panels of FIG. 9 show the results of hematopoietic stem cells cultured in MKLI medium containing TPO (50 ng/mL) (note that TPO used herein was purchased from Stem Cell Technologies). Platelets were slightly produced on either one of Day 2 and Day 8 after initiation of culture of the hematopoietic stem cells. The ratio of CD41 positive cells on Day 8 was 5.56%, which was increased from the ratio (1.26%) in hematopoietic stem cells before culture but was not as high as the ratio obtained by using the culture supernatant of preadipocytes and shown in the upper-stage panel of FIG. 9.

The lower-stage panels of FIG. 9 show the results of hematopoietic stem cells cultured in TPO-free MKLI medium, "MKLI medium-TPO". Platelets were produced on neither Day 2 nor Day 8 after initiation of culture of the hematopoietic stem cells. Dead cells were detected and CD41 positive cells were not observed, either.

From the above results, it has been demonstrated that TPO secreted during the process of producing platelets from preadipocytes has an activity (TPO desired to have) for inducing differentiation of hematopoietic stem cells into megakaryocytes/platelets. It has been also demonstrated that the culture supernatant of preadipocytes has an activity for extremely efficiently inducing differentiation of hematopoietic stem cells into megakaryocytes/platelets.

Example 11

[Transferrin Receptor Involved in Induction of TPO Production]

A medium was prepared by removing bovine serum albumin, insulin, LDL cholesterol and 2-β-mercaptoethanol from MKLI medium. The medium is the same as a medium ("basic medium+transferrin"), which is prepared by adding 200 µg/mL iron-bound transferrin to a medium (of MKLI medium) corresponding to a basic medium (a medium prepared by adding, to Iscove's Modified Dulbecco's Medium, IMDM), 2 mM L-glutamine, a 100 U/mL penicillin-streptomycin solution, and nucleotides (ATP, UTP, GTP, and CTP, 20 µM for each) and corresponding to a medium prepared by adding 200 μg/mL iron-bound transferrin to "the particularly preferable basic medium in the present invention" described in the detailed description of the present application.

To preadipocytes, a gene of siRNA of transferrin receptor CD71 (siRNA-CD71) (the sequence of a sense strand is represented by SEQ. ID No. 1, whereas the sequence of the antisense strand is represented by SEQ. ID No. 2) or a scrambled oligo (negative control) (the sequence of a sense strand is represented by SEQ. ID No. 3, whereas the sequence of the antisense strand is represented by SEQ. ID No. 4) was introduced. The resultant preadipocytes were cultured in the aforementioned "basic medium+transferrin". TPO in each of the culture supernatants was measured by ELISA quantitation using the TPO Quantikine ELISA kit (manufactured by R&D Systems). The results are shown in Table 6. In Table 6, "unmeasurable" means that measurement values are equivalent to the value of the background. As is apparent from Table 6, TPO was secreted from preadipocytes using the scrambled oligo, whereas TPO was not secreted from preadipocytes in which transferrin receptor CD71 was knocked down by siRNA. From this, it was clearly demonstrated that it is necessary to induce TPO production by way of a transferrin receptor.

TABLE 7

| | TPO (pg/mL) | | |
|---|---|---|---|
| | Day 0 | Day 4 | Day 8 |
| 1) MKLI medium-TPO | Below detection limit | 69.4 ± 2.0 | 36.1 ± 5.8 |
| 2) Basic medium + iron-bound transferrin | Below detection limit | 49.4 ± 11.3 | 44.4 ± 4.2 |

From the results of Table 7, in the case of using "basic medium+iron-bound transferrin", TPO concentration of the culture on Day 4 was lower than that of the case of using "MKLI medium-TPO"; however, the level of TPO close to Day 4 was maintained even on Day 8 and higher than the case of using "MKLI medium-TPO".

Example 13

[Investigation on the Concentration of Iron-Bound Transferrin]

Human preadipocytes maintenance-cultured in accordance with the method of Example 9 were prepared and

TABLE 6

| | Day 0 (48 hours after SiRNA introduction) | | Day 2 | | Day 4 | |
|---|---|---|---|---|---|---|
| | CD71 % | TPO pg/mL | CD71 % | TPO pg/mL | CD71 % | TPO pg/mL |
| siRNA-CD71 | 5.7 ± 0.2 | Unmeasurable | 13.7 ± 0.6 | Unmeasurable | 7.5 ± 0.7 | Unmeasurable |
| Negative control | 14.5 ± 0.3 | Unmeasurable | 32.0 ± 0.1 | 6.7 ± 2.9 | 5.7 ± 0.2 | 46.2 ± 17.8 |

Example 12

[Comparison of TPO Production Between the Case of Using "MKLI Medium-TPO" and the Case of Using "Basic Medium+Iron-Bound Transferrin"]

Human preadipocytes were cultured in 1)"MKLI medium-TPO" or 2) the aforementioned "basic medium+ iron-bound transferrin" (containing 200 μg/mL iron-bound transferrin) at 37° C. for 8 days. The TPO concentration in each of the culture supernatants was measured immediately after initiation of culture (Day 0), Day 4, and Day 8 after initiation of culture of the human preadipocytes by ELISA quantitation using the TPO Quantikine ELISA kit (manufactured by R&D Systems). The results are shown in Table 7.

cultured in a medium prepared by adding iron-bound transferrin different in concentration to the basic medium described in Example 11. The ratio (%) of CD41 (specific marker of megakaryocytes/platelets)-positive cells on Day 4 after initiation of culture was determined. The results are shown in Table 8.

TABLE 8

| | Iron-bound transferrin(μg/mL) | | | | | |
|---|---|---|---|---|---|---|
| | 0 | 25 | 50 | 100 | 200 | 400 |
| TPO (pg/mL) | Below measurement limit | Below measurement limit | 7.5 ± 1.1 | 10.8 ± 3.5 | 10 ± 2.4 | Below measurement limit |

From the results, it has been demonstrated that even if the concentration of iron-bound transferrin is lower than that (200 μg/mL) of the conventional MKLI medium, more specifically, even if the iron-bound transferrin concentration is 100 μg/mL, TPO is produced in a concentration equal to or greater than the case of 200 μg/mL, and that even if the concentration of iron-bound transferrin is 50 μg/mL, the concentration of TPO produced decreased by about 25% compared to the case of 200 μg/mL.

Example 14

[TPO Production Associated with Differentiation Induction of Mesenchymal Cells Such as Preadipocytes into Megakaryocytes/Platelets]

From the results of Example 9 and others, it has been successfully confirmed that TPO is secreted in a culture supernatant during the differentiation process of preadipocytes into megakaryocytes/platelets. Then, to find the cells producing and secreting TPO, expression of TPO gene before and after differentiation induction of mesenchymal cells including preadipocytes into megakaryocytes/platelets was checked. Specifically, human and mouse primary-culture preadipocytes described in Example 9 and established mouse bone marrow mesenchymal stem cells (HS-22, purchased from the JCRB cell bank of the National Institute of Biomedical Innovation), bone marrow stromal cells (OP9, provided by Graduate Schools of Osaka University) and mouse preadipocytes (3T3-L1, purchased from the JCRB cell bank of the National Institute of Biomedical Innovation) were used. These cells were all subjected to differentiation induction into megakaryocytes/platelets using a differentiation-inducing medium ("MKLI medium-TPO").

Gene expression of TPO was analyzed by subjecting mesenchymal cells before differentiation induction and megakaryocytes/platelets after differentiation induction to real time PCR method. First, RNA was extracted from these cells by use of guanidinium thiocyanate-phenol-chloroform (trade name TRIzol, manufactured by Life Technology). and subjected to reverse transcription reaction by use of QuantiTect Reverse Transcription (manufactured by QIAGEN Genomics Inc.). Subsequently, the obtained cDNA was subjected to quantification expression analysis using probes of TPO and endogenous control GAPDH purchased from TaqMan (registered trademark) Gene Expression Assays (manufactured by Life Technology) Of these probes, TPO: Hs01061346_m1 and GAPDH: Hs02758991_g1 were used for analysis for human cell types; and TPO: Mm00437040_m1 and GAPDH: Mm99999915_g1 were used for mouse cell types. Measurement was performed by 7500 Fast real time PCR system (manufactured by Life Technology) and the obtained data were corrected based on the value of endogenous control, GAPDH. The results of the primary culture cells are shown in Table 9 and the results of the established cells are shown in Table 10.

TABLE 9

| | TPO mRNA | | |
|---|---|---|---|
| | Before differentiation induction | Day 5 | Day 8 |
| Human preadipocytes (HPAd) | 16.5 ± 0.8 | 15.9 ± 0.6 | 16.0 ± 0.5 |
| Mouse preadipocytes (derived from subcutaneous adipose tissue) | 13.8 ± 0.4 | 13.2 ± 0.5 | 13.9 ± 0.1 |

TABLE 10

| | TPO mRNA | |
|---|---|---|
| | Before differentiation induction | Day 6 |
| Mesenchymal cells (HS-22) | 16.5 ± 0.5 | 11.8 ± 0.1 |
| Stromal cells (OP9) | 11.3 ± 0.4 | 8.9 ± 0.0 |
| Preadipocytes (3T3-L1) | 13.4 ± 0.1 | 12.7 ± 0.1 |

From these results, it has been clearly demonstrated that TPO mRNA is expressed in mesenchymal cells including preadipocytes and megakaryocytes/platelets differentiated from these cells.

Total RNA was extracted from the cells obtained by culturing human preadipocytes in "MKLI medium-TPO". The extraction was performed by the guanidinium thiocyanate-phenol-chloroform method using TRizol (manufactured by Life Technology). Using QuaniTect Reverse Transcription kit (manufactured by QIAGEN Genomics Inc.), cDNA was synthesized from the RNA extracted. PCR was performed by using the resultant cDNA as a template and the PCR product was subjected to nucleotide sequencing. The nucleotide sequence thereof coincided with the known nucleotide sequence of human TPO (accession number NM_000460).

These results support that mesenchymal cells produce TPO during the differentiation process thereof into megakaryocytes/platelets and secrete TPO in the supernatant.

Example 15

[Establishment of Preadipocytes and Production of Platelets and TPO from Established Preadipocytes]

Preadipocytes were established. To check whether or not the established preadipocytes can produce platelets and TPO, the following experiment was carried out. Note that establishment of preadipocytes will be described in the following Section (1) and establishment of CD31 negative, CD71 positive and c-MPL positive preadipocytes will be described in the following Section (2).

(1) Establishment of Preadipocytes

DMEM medium (Dulbecco's Modified Eagle's Medium, manufactured by Life Technology) containing 10% fetal bovine serum (FBS) (manufactured by Sigma) was prepared and used as a preadipocyte culturing basic medium. A preadipocyte culturing basic medium containing a differentiation-inducing agent was prepared by adding differentiation-inducing agents for matured adipocytes, i.e., 3-isobutyl-1-methylxanthin (IBMX) (manufactured by Sigma), insulin (Sigma), dexamethasone (manufactured by Sigma) and indomethacin (manufactured by Sigma) to the preadipocyte culturing basic medium. As the concentrations of the differentiation-inducing agents, the concentration of IBMX was 500 μM, insulin 1.6 μM, dexamethasone 1 μM and indomethacin 200 μM.

In the preadipocyte culturing basic medium containing a differentiation-inducing agent placed in a culture plate, human preadipocytes were cultured at 37° C., in 5% $CO_2$ concentration conditions for 14 days. After culture, cells (mature adipocytes) were removed from the culture plate with trypsin. To the cells, trypsin and the aforementioned preadipocyte culturing basic medium were added. The resultant mixture was centrifuged and cells (mature adipocytes) suspended in the supernatant were collected. In a culture flask sufficiently filled with 20% FBS-containing DMEM medium, the mature adipocyte collected were placed and cultured while suspending the mature adipocytes so as to be in contact with the upper (inward) surface of the culture flask filled with medium (so-called "ceiling culture"). The ceiling culture was carried out at 37° C. in 5% $CO_2$ concentration conditions for 7 days. Thereafter, the medium in the culture flask was discharged and reduced down to about ¼ in volume and the cells were cultured at 37° C. in 5% $CO_2$ concentration conditions for 7 days in such a state that the cells were allowed to attach on the bottom of the culture flask. In this manner, preadipocytes were established. The established preadipocytes thus obtained were subcultured in the preadipocyte culturing basic medium.

(2) Establishment of CD31 Negative, CD71 Positive and c-MPL Positive Preadipocytes CD31 negative, CD71 positive and c-MPL positive preadipocytes were separated from human preadipocytes by flow cytometry (see, Example 8) using FACS. The preadipocyte culturing basic medium containing a differentiation-inducing agent placed in a culture plate (see Example 15, Section (1)) was prepared. In the medium, "preadipocytes immediately after separation", or "preadipocytes cultured in the preadipocyte culturing basic medium after separation" were cultured at 37° C. in 5% $CO_2$ concentration conditions for 14 days. After the culture, cells (mature adipocytes) were removed from the culture plate with trypsin. To the cells, trypsin and the aforementioned preadipocyte culturing basic medium were added. The resultant mixture was centrifuged and cells (mature adipocytes) suspended in the supernatant were collected. In a culture flask sufficiently filled with 20% FBS-containing DMEM medium, the mature adipocytes collected were placed and cultured while suspending the mature adipocytes so as to be in contact with the upper (inward) surface of the culture flask filled with medium (so-called "ceiling culture"). The ceiling culture was carried out at 37° C. in 5% $CO_2$ concentration conditions for 7 days. Thereafter, the medium in the culture flask was discharged and reduced down to about ¼ in volume and the cells were cultured at 37° C. in 5% $CO_2$ concentration conditions for 7 days in such a state that the cells were allowed to attach on the bottom of the culture flask. In this manner, preadipocytes were established. The established preadipocytes thus obtained were subcultured in the preadipocyte culturing basic medium.

The established preadipocytes obtained in Example 15, Section (1) or (2) were induced to differentiate into megakaryocytes/platelets by the method described in Example 1. As a result, it has been successfully confirmed that megakaryocytes and platelets are produced similarly to Example 1. These established preadipocytes were induced to differentiate into megakaryocytes/platelets in accordance with the method described in Example 10. As a result, it has been confirmed that TPO is produced similarly to Example 10.

Example 16

[Production of TPO During Differentiation Process from Preadipocytes to Mature Adipocytes]

To check whether TPO is produced during differentiation process from preadipocytes to mature adipocytes, the following experiment was carried out.

In the preadipocyte culturing basic medium containing a differentiation-inducing agent in Example 15, human preadipocytes were cultured at 37° C. in 5% $CO_2$ concentration conditions for 14 days. The concentration of TPO in the culture supernatant was measured by ELISA quantitation using the TPO Quantikine ELISA kit (manufactured by R&D System). As a result, the concentration of TPO in the culture supernatant immediately after initiation of culture (Day 0) was below a detection limit, whereas the concentration of TPO in the culture supernatant on Day 14 after initiation of culture was 51.5±21.9 pg/mL. From the results, it has been clearly demonstrated that preadipocytes are stimulated to differentiate into mature adipocytes, and secretion of TPO is induced during the differentiation process.

INDUSTRIAL APPLICABILITY

According to the first invention, it is possible to provide a more practical megakaryocyte and/or platelet production method, enabling to produce megakaryocytes having platelet producibility and/or platelets having thrombus forming ability from mesenchymal cells such as preadipocytes in a relatively short period of time, simply, in a large amount, at lower cost and more efficiently in vitro. According to the second and third inventions, it is possible to provide a method for producing TPO having an ability to induce/promote platelet production easily and in a large amount.

The invention claimed is:

1. A method for producing a megakaryocyte and/or platelet, comprising culturing a mesenchymal cell in a mesenchymal cell culturing basic medium containing an iron ion and an iron transporter so that the mesenchymal cell differentiates into a megakaryocyte and/or platelet, and collecting the megakaryocyte and/or platelet from a culture,
wherein the mesenchymal cell is a CD31 negative and CD71 positive mesenchymal cell and wherein the medium does not contain exogenous thrombopoietin.

2. The production method according to claim 1, wherein the CD31 negative and CD71 positive mesenchymal cell is further positive for myeloproliferative leukemia protein (c-MPL).

3. The production method according to claim 1, wherein the iron transporter is transferrin.

4. The production method according to claim 1, wherein the iron ion and iron transporter are an iron-bound transferrin.

5. The production method according to claim 1, wherein the culturing is performed for 5 to 17 days.

6. The production method according to claim 1, wherein more than one megakaryocyte and/or platelet is produced from one or more mesenchymal cells which are CD31 negative and CD71 positive, and wherein a yield of the megakaryocyte and/or platelet is 270-1,080% relative to the one or more mesenchymal cells initially prepared.

7. The production method according to claim 1, wherein more than one platelet is produced from one or more mesenchymal cells which are CD31 negative and CD71 positive, and wherein a percentage of platelets contributing to thrombus formation as measured by thrombus formation analysis of the platelets is 70% to 85%.

8. The production method according to claim 1, further comprising a step of purifying the megakaryocyte and/or platelet from the culture.

9. The production method according to claim 2, wherein the iron transporter is transferrin.

10. The production method according to claim 2, wherein the iron ion and iron transporter are an iron-bound transferrin.

11. The production method according to claim 2, wherein the culturing is performed for 5 to 17 days.

12. The production method according to claim 1, wherein the culturing of the mesenchymal cell does not involve culturing a hematopoietic stem cell.

13. The production method according to claim 1, further comprising a step of screening a plurality of mesenchymal cells for expression of the cell-surface marker CD71, thereby generating a population of mesenchymal cells that includes a higher ratio of CD71-positive mesenchymal cells relative to the initial plurality of mesenchymal cells, and culturing the population with the basic medium.

* * * * *